US010226467B2

(12) United States Patent
Artero Allepuz et al.

(10) Patent No.: US 10,226,467 B2
(45) Date of Patent: *Mar. 12, 2019

(54) COMPOUNDS FOR THE TREATMENT OF MYOTONIC DYSTROPHY

(71) Applicants: UNIVERSITAT DE VALÈNCIA, València (ES); INSTITUT QUÍMIC DE SARRIÀ CETS FUNDACIÓ PRIVADA, Barcelona (ES); INSTITUT UNIV. DE CIÈNCIA I TECNOLOGIA, S.A., Mollet del Valles (ES)

(72) Inventors: Ruben Artero Allepuz, València (ES); Josep Castells Boliart, Mollet del Valles (ES); José Ignacio Borrell Bilbao, Barcelona (ES); Beatriz Llamusi Troísi, València (ES); Ariadna Bargiela Schönbrunn, València (ES); Piotr Konieczny, València (ES); Marta Pascual Gilabert, Mollet del Valles (ES); Jordi Teixidó Closa, Barcelona (ES); Roger Estrada Tejedor, Barcelona (ES); Alejandro López González, Barcelona (ES)

(73) Assignees: Universitat de Valencia, Valencia (ES); Institut Quimic de Sarria Cets Fundacio Privada, Barcelona (ES); Institut Univ. de Ciencia I Tecnologia, S.A., Mollet del Valles (ES)

( * ) Notice: Subject to any disclaimer, the term of this patent is extended or adjusted under 35 U.S.C. 154(b) by 0 days.

This patent is subject to a terminal disclaimer.

(21) Appl. No.: 15/526,188

(22) PCT Filed: Nov. 13, 2015

(86) PCT No.: PCT/EP2015/076547
§ 371 (c)(1),
(2) Date: May 11, 2017

(87) PCT Pub. No.: WO2016/075285
PCT Pub. Date: May 19, 2016

(65) Prior Publication Data
US 2017/0312285 A1 Nov. 2, 2017

(30) Foreign Application Priority Data

Nov. 14, 2014 (EP) .................................. 14382449

(51) Int. Cl.
A61K 31/522 (2006.01)
C07D 473/08 (2006.01)
A23L 7/122 (2016.01)
A23C 23/00 (2006.01)
A23G 1/32 (2006.01)
A23L 2/52 (2006.01)
A23C 9/13 (2006.01)
A23C 9/152 (2006.01)

(52) U.S. Cl.
CPC ............ *A61K 31/522* (2013.01); *A23C 23/00* (2013.01); *A23G 1/32* (2013.01); *A23L 2/52* (2013.01); *A23L 7/122* (2016.08); *C07D 473/08* (2013.01); *A23C 9/13* (2013.01); *A23C 9/152* (2013.01); *A23V 2002/00* (2013.01)

(58) Field of Classification Search
None
See application file for complete search history.

(56) References Cited

U.S. PATENT DOCUMENTS

| 8,741,572 B1 | 6/2014 | Friesen et al. |
| 8,754,084 B2 | 6/2014 | Zimmerman et al. |
| 2011/0269665 A1 | 11/2011 | Kole |
| 2014/0051709 A1 | 2/2014 | Reddy et al. |

FOREIGN PATENT DOCUMENTS

| EP | 2554180 | 2/2013 | |
| EP | 2560001 | 2/2013 | |
| EP | 2742974 | 6/2014 | |
| JP | 09227561 | 9/1997 | |
| WO | WO2003/020977 | 3/2003 | |
| WO | WO-2006127930 A2 * | 11/2006 | ........... A61K 31/365 |
| WO | 2017/180976 | 10/2017 | |
| WO | 2017/197107 | 11/2017 | |
| WO | 2018/051355 | 3/2018 | |

OTHER PUBLICATIONS

Campbell, Craig. J Neurol Neurophysiol (2012) 1-8.*
The Muscular Dystrophy Association. MDA. Adult Onset MMD1 and MMD2 (2017) Web <https://www.mda.org/disease/myotonic-muscular-dystrophy/signs-and-symptoms/adult-onset-MMD>.*
Franco, Rafael. Nutrients (2013), 5, 4159-4173.*
Itahara, T. and Imamura, K., "Preparation and NMR Study of 7,7'-(alpha,omega-Alkanediyl)bis[theophylline], 1,1'(alpha,omega-Alkanediyl)bis[theobromine], and 1,1'-(alpha,omega-Alkanediyl)bis[3-methyluracil]," Bull. Chem. Soc. Jpn., 1994, 67, 203-209.
Keller, C., "Congenital myotonic dystrophy requiring prolonged endotracheal and noninvasive assisted ventilation: not a uniformly fatal condition," Pediatrics, American Academy of Pediatrics, 1998, 101, 704-706.
Lee, S. et al., "Survival of a 30-week baby with congenital myotonic dystrophy initially ventilated for 55 days," Journal of Paediatrics and Child Health, 1999, 35, 313-314.

(Continued)

Primary Examiner — Deepak R Rao
Assistant Examiner — Laura M Daniel
(74) Attorney, Agent, or Firm — Barnes & Thornburg LLP

(57) ABSTRACT

The present invention relates to a compound of formula (I), provided that this compound is not caffeine, for use in the treatment of myotonic dystrophy type 1 and type 2. The present invention also relates to compositions comprising the compound of formula (I). The present invention further relates to new compounds which are dimers of compounds of formula (I).

18 Claims, 5 Drawing Sheets

(56) References Cited

OTHER PUBLICATIONS

Gruener, R. et al., "Caffine-Modulated Acetylcholine Sensitivity in Denervated Rat and Diseased Human Muscle," Life Sciences, 1975, 17, 1557-1566.

Rutherford, M. et al., "Congenital myotonic dystrophy: respiratory function at birth determines survival," Archives of Disease in Childhood, 1989, 64, 191-195.

PCT Search Report and Written Opinion for PCT/EP2015/076547, completed Feb. 3, 2016.

Campbell, Craig, "Congenital Myotonic Dystrophy," 2012, Journal of Neurology & Neurophysiology, No. S7, pp. 1-8.

Rutherford, M. A., et al., "Congenital Myotonic Dystrophy: Respiratory Function at Birth Determines Survival," 1989, Disease in Childhood, No. 64, pp. 191-195.

Chamberlain, Chrisopher M., et al., "Mouse Model of Muscleblind-Like 1 Overexpression: Skeletal Muscle Effects and Therapeutic Promise," 2012, Human Molecular Genetics, vol. 21, No. 21, pp. 4645-4654.

Childs-Disney, Jessica L., et al., "Induction and Reversal of Myotonic Dystrophy Type 1 Pre-mRNA Splicing Defects by Small Molecules," 2013, Nature Communications, vol. 4, No. 2044, pp. 1-11.

Coonrod, Leslie A., et al., "Reducing Levels of Toxic RNA with Small Molecules," 2013, American Chemical Society, No. 8, pp. 2528-2537.

Franco, Rafael, et al., "Health Benefits of Methylxanthines in Cacao and Chocolate," 2013, Nutrients, No. 5, pp. 4159-4173.

Garcia-Lopez, Amparo, et al., "In Vivo Discovery of a Peptide that Prevents CUG-RNA Hairpin Formation and Reverses RNA Toxicity in Myotonic Dystrophy Models," 2011, PNAS, vol. 108, No. 29, pp. 1186-11871.

Gareiss, Peter C., et al., "Dynamic Combinatorial Selection of Molecules Capable of Inhibiting the (CUG) Repeat RNA-MBNL1 Interaction In Vitro: Discovery of Lead Compounds Targeting Myotonic Dystrophy (DM1)," 2008, J. Am. Che. Soc., vol. 130, No. 48, pp. 16254-16261.

Gomes-Pereira, Mario, et al., "Myotonic Dystrophy Mouse Models: Towards Rational Therapy Development," 2011, Trends in Molecular Medecine, vol. 17, No. 9, pp. 506-517.

Gomes-Pereira, Mario, et al., "Chemically Induced Increases and Decreases in the Rate of Expansion of a CAG-CTG Rriplet Repeat," 2004, Nucleic Acids Research, vol. 32, No. 9, pp. 2865-2872.

Henderson-Smart, D.J., et al., "Prophylactic Methylxanthine for Prevention of Apnoea in Preterminfants (Review)." 2010, Cochrane Database of Systematic Reviews, Issue 10, pp. 1-3.

Hoskins, Jason W., et al., "Lomofungin and Dilomofungin: Inhibitors of MBNL1-CUG RNA Binding with Distinct Cellular Effects," 2014, Nucleic Acids Research, vol. 42, No. 10, pp. 6591-6602.

Huin, Vincent, et al., "MBNL1 Gene Variants as Modifiers of Disease Severity in Myotonic Dystrophy Type 1," 2013, J. Neurol., No. 260, pp. 998-1003.

Jahromi, Amin Haghighat, et al., "A Novel CUGexp-MBNL1 Inhibitor with Therapeutic Potential for Myotonic Dystrophy Type 1," 2013, ACS Chem. Biol., No. 8, pp. 1037-1043.

Kanadia, Rahul N., et al., "Reversal of RNA Missplicing and Myotonia after Muscleblind Overexpression in a Mouse Poly(CUG) Model for Myotonic Dystrophy," 2013, PNAS, vol. 103, No. 31, pp. 11748-11753.

Parkesh, Raman, et al., "Design of a Bioactive Small Molecule That Targets the Myotonic Dystrophy Type 1 RNA via an RNA Motif-Ligand Database and Chemical Similarity Searching," 2012, J. Am. Chem. Soc., No. 134, pp. 4731-4742.

Scanlon, J. E. M., et al., "Caffeine or Theophylline for Neonatal Apnoea," 1992, Archives of Disease in Childhood, No. 67, pp. 425-428.

Statland, Jeffrey M., et al., "Mexiletine for Symptoms and Signs of Myotonia in Non-Dystrophic Myotonia: A Randomized Controlled Trial," 2013, JAMA, No. 13, pp. 1357-1365.

Suominen, Tiina, et al., "Population Frequency of Myotonic Dystrophy: Higher Than Expected Frequency of Myotonic Dystrophy Type 2 (DM2) Mutation in Finland," 2011, European Journal of Human Genetics, No. 19, pp. 776-782.

Warf, M. Bryan, et al., "Pentamidine Reverses the Splicing Defects Associated with Myotonic Dystrophy," 2009, PNAS, vol. 106, No. 44, pp. 18551-18556.

Wong, Chun-Ho, "Targeting Toxic RNAs that Cause Myotonic Dystrophy Type 1 (DM1) with a Bisamidinium Inhibitor," 2014, J. Am. Chem. Soc., No. 136, pp. 6355-6361.

Mercuri, Eugenio et al., "Muscular dystrophies," The Lancet, 2013, 381, 845-860.

Sewry, "Muscular dystrophies: an update on pathology and diagnosis," Acta Neuropathol 120:343-358, (2010).

* cited by examiner

COMPOUNDS FOR THE TREATMENT OF MYOTONIC DYSTROPHY

CROSS-REFERENCE TO RELATED APPLICATIONS

This application is a national stage entry under 35 USC § 371 of PCT International Application Number PCT/EP2015/076547, filed 13 Nov. 2015, which claims priority to European Patent Application Number 14382449.8, filed 14 Nov. 2014, the entire disclosures of each of which is expressly incorporated by reference herein.

FIELD OF INVENTION

The present invention relates to the field of rare diseases, in particular the invention relates to myotonic dystrophy. More particularly, the present invention relates to compounds and compositions comprising thereof for use in the treatment of myotonic dystrophy type 1 and type 2. The present invention further relates to new compounds.

BACKGROUND OF THE INVENTION

Myotonic Dystrophy (DM) is the most common form of muscular dystrophy in adults and includes two clinically similar diseases although originating from distinct genetic mutations. DM1 (Steinert's disease) corresponds to the majority of the cases of DM and stems from an expansion of the CTG trinucleotide repeat (typically more than 50 units) in the 3'-untranslated region (UTR) of the DMPK gene whereas DM2 originates from big expansions of the CCTG tetranucleotide in the first intron of the CNBP gene. Both are rare diseases, with a global combined prevalence estimated at 12.5 per 100000, although it has been suggested that it could be three times higher (Suominen, T. et al. Population frequency of myotonic dystrophy: higher than expected frequency of myotonic dystrophy type 2 (DM2) mutation in Finland. Eur J Hum Genet. 19(7):776-82, 2011). DM1 is a multisystemic disease that affects primarily to the skeletal muscle (miotonia, muscle weakness and degeneration), the heart and the central nervous system (Gomes-Pereira, M. et al. Myotonic dystrophy mouse models: towards rational therapy development. Trends Mol Med. 17(9):506-17 (2011)).

Disease severity and age of onset are critically linked to expansion size. Whereas in classic adult onset the approximate number of repeats is 50 to <500, adolescent onset is 500 to <1000, childhood onset is 1000 to <1.500, and congenital onset is equal or superior to 1500. Due to these differences, currently, there is not clear if the pathogenesis of congenital DM1 (CDM) is similar to adult DM1. In fact, unknown factors account for the unique features of CDM as there is no animal model of DM1 that produces a typical CDM phenotype (Campbell, et al. Congenital Myotonic Dystrophy J. Neurol. Neurophysiol. S7-001, XP055186364, 2012)

Cells carrying few CTG repeats show a functional equilibrium between two antagonistic splicing regulators: muscleblind-like 1 (MBNL1) and CUGBP/Elav-like family member 1 (CELF1). The balance between MBNL1 and CELF1 controls the establishment of adult splicing profiles for a subset of developmentally regulated transcripts. The CTG repeat expansion expressed in a DM1 cell forms an imperfect double-stranded stem loop structure that has two main pathogenic consequences: MBNL1 sequestration by RNA foci and protein kinase C (PKC)-mediated and AKT-mediated CELF1 hyperphosphorylation, stabilisation and subcellular redistribution. As a result of MBNL1 depletion and CELF1 upregulation, the balance between these two splicing regulators is disturbed and the alternative splicing of a series of developmentally regulated transcripts reverts to a foetal pattern. The abnormal expression of splicing isoforms in adult skeletal muscle, heart and brain is likely to contribute to the DM1 disease symptoms. Whereas MBNL1 seems critical in skeletal and cardiac phenotypes, sequestration of the MBNL2 paralog has been suggested to originate brain symptoms and MBNL3 may inhibit muscle differentiation. In addition to defective alternative splicing regulation, protein translation deficits, Repeat-Associated non-ATG translation (RAN translation) and bidirectional transcription of the DMPK gene, altered expression of microRNAs, gene transcription deficiencies, and RNA interference, among others, have been shown to contribute to molecular alterations typical of DM in different cell and animal models of the disease.

Under expression of MBNL or over expression of CELF1, or a combination of both situations as exists in human DM1 manifests in a multisystem illness due to modifications of RNA splicing.

DM1 is a truly multisystem disorder, primarily affecting skeletal muscles (myotonia, muscle weakness and degeneration), the heart and the central nervous system (CNS) (Gomes-Pereira, M. et al. Myotonic dystrophy mouse models: towards rational therapy development. Trends Mol Med. 17(9):506-17 (2011)). The great variability of DM1 symptoms and age of onset results in three main clinical forms of the disease: late-onset, classical adult onset and congenital DM1. DM1 can occur in patients of any age whereas DM2 typically presents in adults. Both DM1 and DM2 patients can also be considered as a person who carries the expanded CTG or CCTG mutation, respectively.

Myotonia (delayed muscle relaxation after initial contraction) and progressive wasting of distal muscles are prominent features of DM1 in skeletal muscle. The more severe congenital form of DM1 is characterized by general muscle hypotonia and respiratory distress at birth, as well as delayed motor development.

A large portion of patients suffer from cardiac conduction blocks, detected by electrocardiogram (ECG), and cardiac histological abnormalities. Progressive cardiopathy can result in complete atrioventricular block or ventricular arrhythmias and subsequent sudden death in almost 30% of DM1 patients. Particularly, problems related to the cardiopulmonary system accounts for 70% deaths due to DM1.

CNS manifestations are highly debilitating and support the view that DM1 is also a brain disorder. DM1 neuropsychological dysfunction is accompanied by histological abnormalities, as well as brain structural changes and altered metabolism.

The impact of DM1 further affects a variety of tissues and results in presenile cataracts, abnormal glucose tolerance and hyperinsulinism, gastrointestinal dysfunction and testicular atrophy. See Gomes-Pereira et al. Trends in Molecular Medicine, 2011, 17(9), 506-516

According to the Myotonic Dystrophy Foundation (http://www.myotonic.org), the symptomatology of the myotonic dystrophy can be expressed by the following events 1. Skeletal muscle: myotonia, progressive wasting and weakness, pain, general hypotonia in congenital DM1
2. Heart: cardiac condition defects, prolonged PR intervals, first degree atrioventricular block, arrhythmias
3. Central nervous system: hypersomnolence, cognitive impairment, executive dysfunction, visual-spacial memory deficits, neuropsychological changes, mental retardation in congenital DM1

4. Smooth muscle: gastrointestinal complications, swallowing issues, abdominal pain, abnormal motility, malabsorption, constipation/diarrhea, anal incontinence
5. Respiratory system: breathing problems in newborns, frequent lung infections, aspiration of food or fluids into airways, inability to breathe in enough oxygen, sleep apnea
6. Hormonal system: hyperinsulinism (diabetes), male prefrontal balding
7. Immune system: hypogammaglobulinemia.
8. Vision: premature subcapsular iridescent and muticoloured cataracts, damage to the retina, drooping eyelids (ptosis)
9. Reproductive system: testicular atrophy, small testes, reduced fertility, low sperm count, low testosterone, higher risk of miscarriage and stillbirth, early menopause, problems with pregnancy and delivery, newborn complications, more severe with each generation ("anticipation")
10. Skin: Higher risk of benign skin tumor (pilomatrixoma)

Current therapeutic strategies are based on candidate drugs that bind to CUG or CCUG repeats, thereby releasing MBNL proteins to regulate splicing, or other processes, of its pre-mRNA targets. An increase in free MBNL1 protein has been shown to reduce the severity of symptoms in animal models of DM1, while in contrast, a decrease of free MBNL1 protein is observed with longer expansions, which are correlated with more severe disease. The pathogenic role of the MBNL1 gene is further substantiated by the fact that MBNL1 gene variants modify DM1 severity (Vincent Huin et al. *MBNL1 gene variants as modifiers of disease severity in myotonic dystrophy type* 1. J Neurol (2013) 260:998-1003). Similarly, MBNL proteins have been shown to get sequestered in DM2, thus, strategies aimed at increasing steady state levels of these proteins have the potential to become treatments for DM2. Then, the consensus strategy to reverse splicing abnormalities observed in DM1 and DM2, among other molecular alterations, is based in a reduction in nuclear foci and the concomitant reduction in nuclear sequestration of MBNL proteins. Warf and colleagues (Warf, M., Nakamori, M., Matthys, C. Thornton, C. and Berglund, J. (2009) Pentamidine reverses the splicing defects associated with myotonic dystrophy. Proceedings of the National Academy of Sciences of the United States of America, 106, 18551-18556. Coonrod, L., et al. (2013) Reducing levels of toxic RNA with small molecules. ACS Chem Biol. 8(11):2528-37) demonstrated that pentamidine facilitates a partial rescue of DM1 pathology.

Since then, some other therapies have been disclosed, such as antisense oligonucleotide compounds (see, EP 2 560 001A2, US 2011/0269665 A1), pentamidine analogues (see, A., Haley, M., Thornton, C. et al. (2013) Reducing levels of toxic RNA with small molecules. ACS chemical biology, 8, 2528-2537; Parkesh, R., Childs-Disney, J., Nakamori, M., Kumar, A., Wang, E., Wang, T., Hoskins, J., Tran, T., Housman, D., Thornton, C. et al. (2012) Design of a Bioactive Small Molecule That Targets the Myotonic Dystrophy Type 1 RNA via an RNA Motif-Ligand Database and Chemical Similarity Searching. Journal of the American Chemical Society, 134, 4731-4742), peptides (see, EP 2 554 180 A1, Gareiss, P., Sobczak, K., McNaughton, B., Palde, P., Thornton, C. and Miller, B. (2008) Dynamic combinatorial selection of molecules capable of inhibiting the (CUG) repeat RNA-MBNL1 interaction in vitro: discovery of lead compounds targeting myotonic dystrophy (DM1). Journal of the American Chemical Society, 130, 16254-16261; Garcia-Lopez, A., Llamusi, B., Orzaez, M., Perez-Paya, E. and Artero, R. (2011) In vivo discovery of a peptide that prevents CUG-RNA hairpin formation and reverses RNA toxicity in myotonic dystrophy models. Proceedings of the National Academy of Sciences of the United States of America, 108, 11866-11871), or chemical drug candidates (see, U.S. Pat. No. 8,754,084 B2, EP 2 742 974 A1, U.S. Pat. No. 8,741,572 B1, US 2014/0051709 A1, Jahromi, A. H., Nguyen, L., Fu, Y., Miller, K. A., Baranger, A. M. and Zimmerman, S. C. (2013) A novel CUG(exp). MBNL1 inhibitor with therapeutic potential for myotonic dystrophy type 1. ACS chemical biology, 8, 1037-1043; Wong, C. H., Nguyen, L., Peh, J., Luu, L. M., Sanchez, J. S., Richardson, S. L., Tuccinardi, T., Tsoi, H., Chan, W. Y., Chan, H. Y. et al. (2014) Targeting Toxic RNAs that Cause Myotonic Dystrophy Type 1 (DM1) with a Bisamidinium Inhibitor. Journal of the American Chemical Society, 136, 6355-6361; Childs-Disney, J., Stepniak-Konieczna, E., Tran, T., Yildirim, I., Park, H., Chen, C., Hoskins, J., Southall, N., Marugan, J., Patnaik, S. et al. (2013) Induction and reversal of myotonic dystrophy type 1 pre-mRNA splicing defects by small molecules. Nature communications, 4, 2044; Hoskins, J. W., Ofori, L. O., Chen, C. Z., Kumar, A., Sobczak, K., Nakamori, M., Southall, N., Patnaik, S., Marugan, J. J., Zheng, W. et al. (2014) Lomofungin and dilomofungin: inhibitors of MBNL1-CUG RNA binding with distinct cellular effects. Nucleic acids research, 42, 6591-6602).

The generic cardiovascular drug mexiletine, initially developed to treat heart rhythm abnormalities, has been reported to hold some potential for treating muscle stiffness and other symptoms of non-dystrophic myotonias (NDMs). Mexiletine-induced sodium channel blockade reduced myotonia in small studies (Stantland, J M, et al. Mexiletine for symptoms and signs of myotonia in nondystrophic myotonia: a randomized controlled trial, *JAMA*. 2012, 308(13), 1357-1365).

Therefore, although DM1 was first described in 1909, there is presently no cure or specific treatment for myotonic dystrophy. All the treatments applied are palliative and contribute to control the development of a subset of the overall plethora of symptoms, and the clinical focus is on managing the complications of the disease, but in no case for treating the disease in a definitive manner.

Therefore, there is an existing need for compounds and compositions which can treat myotonic dystrophy, in particular myotonic dystrophy type 1 and type 2, in a more effective way.

The present inventors have surprisingly found that the compounds described herein cover this existing need. In addition, the compounds disclosed herein can be advantageously found directly in natural products or can be readily synthesized in just a few chemical steps.

Some of the compounds described herein are known by those skilled in the art as derivatives of xanthine (known collectively as xanthines or methylxanthines). Methylated xanthines (methylxanthines), include caffeine, aminophylline, IBMX, paraxanthine, pentoxifylline, theobromine, and theophylline. This group of alkaloids that mainly act as adenosine receptor blockers, is commonly used as mild stimulants and as bronchodilators, notably in the treatment of asthma symptoms. In contrast to other more potent stimulants like sympathomimetic amines, xanthines mainly act to oppose the actions of the sleepiness-inducing adenosine, and increase alertness in the central nervous system. They also stimulate the respiratory centre, and are used for treatment of infantile apnea and the apnea of prematurity (AOP). AOP is a common problem affecting premature infants, likely secondary to an immature respiratory system. Methylxanthine therapy is a mainstay of treatment of central apnea by stimulating the central nervous system and respiratory muscle function. The most common cause of apnea specially in newborns is prematurity, to whom the most common drugs used to treat apnea are the methylxanthines (Henderson-Smart et al. Prophylactic methylxanthine for prevention of apnoea in preterm infants. *Cochrane Database Syst Rev.* 2010 Dec. 8; (12):CD000432. doi: 10.1002/14651858.CD000432.pub2), theophylline (Scanlon et al. Caffeine or theophylline for neonatal apnoea? Arch Dis Child. 1992 April; 67(4 Spec No): 425-428) and aminophylline (Larsen et al. Aminophylline versus caffeine citrate for apnea and bradycardia prophylaxis in premature neonates. *Acta Paediatr.* 1995 April; 84(4):360-4).

The inventors have surprisingly found that xanthines are able to increase the amount of free MBNL1 in human DM1 myoblasts. An increase in free MBNL1 protein has been shown to reduce the severity of symptoms in animal models of DM1, while in contrast, a decrease of free MBNL1 protein is observed with longer expansions, which are correlated with more severe disease. The pathogenic role of the MBNL1 gene is further substantiated by the fact that MBNL1 gene variants modify DM1 severity (Vincent Huin et al. MBNL1 gene variants as modifiers of disease severity in myotonic dystrophy type 1. J Neurol (2013) 260:998-1003). Similarly, MBNL proteins have been shown to get sequestered in DM2, thus, strategies aimed at increasing steady state levels of these proteins have the potential to become treatments for DM2

No reference is found in the literature for the direct use of these compounds for the purposes disclosed herein.

SUMMARY OF THE INVENTION

A first aspect of the present invention relates to a compound of formula (I), provided that this compound is not caffeine, for use in the treatment of myotonic dystrophy type 1 and type 2.

A second aspect of the present invention relates to compositions comprising the compound of formula (I) as defined herein.

A third aspect of the present invention relates to new compounds which are dimers of compounds of formula (I).

DETAILED DESCRIPTION OF THE INVENTION

Figure 1:
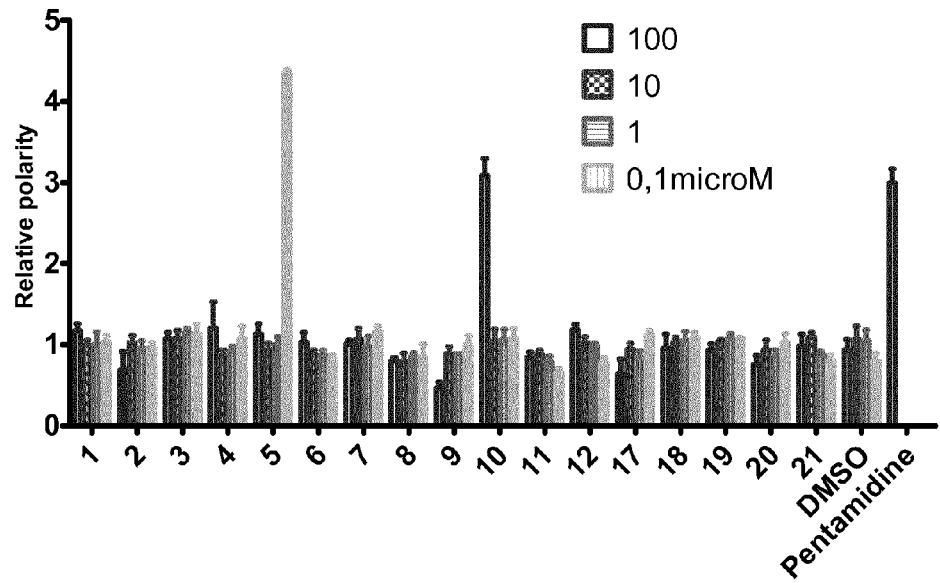
FIG. 1. Polarization measurements relative to the values of polarization of the FAM (CUG) 23 probe without compound. Each of the compounds indicated in the x-axis, was tested at increasing concentrations (from 0.1 to 100 microM). Higher polarization values indicate greater binding capacity to the repeats. Bar graph shows means+s.e.m. from three independent experiments with three technical replicates each.

The present invention relates to a compound of formula (I)

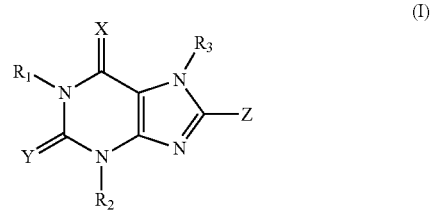

wherein:
$R^1$ is hydrogen; an optionally substituted alkyl chain, preferably optionally substituted methyl, more preferably methyl; an optionally substituted alkenyl; an optionally substituted alkynyl; an optionally substituted cycloalkyl; an optionally substituted cycloalkyl linked to N by an optionally substituted alkyl; an optionally substituted cycloalkyl linked to N by an optionally substituted alkenyl; an optionally substituted cycloalkyl linked to N by an optionally substituted alkynyl; an optionally substituted cycloalkenyl; an optionally substituted cycloalkenyl linked to N by an optionally substituted alkyl; an optionally substituted cycloalkenyl linked to N by an optionally substituted alkenyl; an optionally substituted cycloalkenyl linked to N by an optionally substituted alkynyl; an optionally substituted aryl; an optionally substituted aryl linked to N by an optionally substituted alkyl; an optionally substituted aryl linked to N by an optionally substituted alkenyl; an optionally substituted aryl linked to N by an optionally substituted alkynyl; an optionally substituted heterocycle; an optionally substituted heterocycle linked to N by an optionally substituted alkyl; an optionally substituted heterocycle linked to N by an optionally substituted alkyl; an optionally substituted heterocycle linked to N by an optionally substituted alkenyl; an optionally substituted heterocycle linked to N by an optionally substituted alkynyl chain; $COR^6$; $CONR^6R^7$; $CO_2R^6$; $CSR^6$; $C(S)OR^7$; $CSNR^6R^7$; $SO_2R^6$; $CN$;

$R^2$ is hydrogen; an optionally substituted alkyl chain, preferably optionally substituted methyl, more preferably methyl; an optionally substituted alkenyl; an optionally substituted alkynyl; an optionally substituted cycloalkyl; an optionally substituted cycloalkyl linked to N by an optionally substituted alkyl; an optionally substituted cycloalkyl linked to N by an optionally substituted alkenyl; an optionally substituted cycloalkyl linked to N by an optionally substituted alkynyl; an optionally substituted cycloalkenyl; an optionally substituted cycloalkenyl linked to N by an optionally substituted alkyl; an optionally substituted cycloalkenyl linked to N by an optionally substituted alkenyl; an optionally substituted cycloalkenyl linked to N by an optionally substituted alkynyl; an optionally substituted aryl; an optionally substituted aryl linked to N by an optionally substituted alkyl; an optionally substituted aryl linked to N by an optionally substituted alkenyl; an optionally substituted aryl linked to N by an optionally substituted alkynyl; an optionally substituted heterocycle; an optionally substituted heterocycle linked to N by an optionally substituted alkyl; an optionally substituted heterocycle linked to N by an optionally substituted alkyl; an optionally substituted heterocycle linked to N by an optionally substituted alkenyl; an optionally substituted heterocycle linked to N by an optionally substituted alkynyl; $COR^6$; $CONR^6R^7$; $CO_2R^6$; $CSR^6$; $C(S)OR^7$; $CSNR^6R^7$; $SO_2R^6$; $CN$;

$R^3$ is hydrogen; an optionally substituted alkyl chain, preferably optionally substituted methyl, more preferably methyl; an optionally substituted alkenyl; an optionally substituted alkynyl; an optionally substituted cycloalkyl; an optionally substituted cycloalkyl linked to N by an optionally substituted alkyl; an optionally substituted cycloalkyl linked to N by an optionally substituted alkenyl; an optionally substituted cycloalkyl linked to N by an optionally substituted alkynyl; an optionally substituted cycloalkenyl; an optionally substituted cycloalkenyl linked to N by an optionally substituted alkyl; an optionally substituted cycloalkenyl linked to N by an optionally substituted alkenyl; an optionally substituted cycloalkenyl linked to N by an optionally substituted alkynyl; an optionally substituted aryl; an optionally substituted aryl linked to N by an optionally substituted alkyl; an optionally substituted aryl linked to N by an optionally substituted alkenyl; an optionally substituted aryl linked to N by an optionally substituted alkynyl; an optionally substituted heterocycle; an optionally substituted heterocycle linked to N by an optionally substituted alkyl; an optionally substituted heterocycle linked to N by an optionally substituted alkyl; an optionally substituted heterocycle linked to N by an optionally substituted alkenyl; an optionally substituted heterocycle linked to N by an optionally substituted alkynyl; $COR^6$; $CONR^6R^7$; $CO_2R^6$; $C(S)R^6$; $C(S)OR^6$; $CSNR^6R^7$; $S(O)R^6$; $SO_2R^6$; $SONR^6R^7$; $SO_2NR^6R^7$; a linker attached to another compound of formula (I) through N-7 (the one linked to $R^3$ in structure of formula (I)) wherein the linker is selected from an optionally substituted alkyl, an optionally substituted alkenyl, an optionally substituted alkynyl, an optionally substituted cycloalkyl, an optionally substituted cycloalkenyl, an optionally substituted cycloalkynyl, an optionally substituted alkylcycloalkylalkyl, an optionally substituted alkylcycloalkylalkenyl, an optionally substituted alkylcycloalkylalkynyl, an optionally substituted alkylcycloalkenylalkyl, an optionally substituted alkylcycloalkynylalkyl, an optionally substituted aryl, an optionally substituted alkylarylalkyl, an optionally substituted alkylarylalkenyl, an optionally substituted alkylarylalkynyl, an optionally substituted heterocycle, an optionally substituted alkylheterocycloalkyl, an optionally substituted alkylheterocycloalkenyl, an optionally substituted alkylheterocycloalkynyl;

X is O, NH, S;

Y is O, NH, S independently of X;

Z is hydrogen; an optionally substituted alkyl chain, preferably optionally substituted methyl, more preferably methyl; an optionally substituted alkenyl chain; an optionally substituted alkynyl chain; an optionally substituted cycloalkyl; an optionally substituted cycloalkyl linked through an optionally substituted alkyl; an optionally substituted cycloalkyl linked through an optionally substituted alkenyl; an optionally substituted cycloalkyl linked through an optionally substituted alkynyl chain; an optionally substituted cycloalkenyl; an optionally substituted cycloalkenyl linked through an optionally substituted alkyl; an optionally substituted cycloalkenyl linked through an optionally substituted alkenyl; an optionally substituted cycloalkenyl linked through an optionally substituted alkynyl chain; an optionally substituted aryl; an optionally substituted aryl linked through an optionally substituted alkyl; an optionally substituted aryl linked through an optionally substituted alkenyl; an optionally substituted aryl linked through an optionally substituted alkynyl chain; an optionally substituted heterocycle; an optionally substituted heterocycle linked through an optionally substituted alkyl; an optionally substituted heterocycle linked through an optionally substituted alkyl; an optionally substituted heterocycle linked through an optionally substituted alkenyl; an optionally substituted heterocycle linked through an optionally substituted alkynyl chain; OH; SH; $NH_2$; halogen; $OR^6$; $SR^6$; $NR^6R^7$; CN; $N_3$; $COR^6$; $CONR^6R^7$; $CO_2R^6$; $C(S)R^6$; $C(S)OR^6$; $CSNR^6R^7$; $OCONR^6R^7$; $OCO_2R^6$; $OC(S)R^6$; $OC(S)OR^6$; $NHCONR^6R^7$; $NHCOR^6$; $NHCO_2R^6$; $NHC(S)OR^6$; $S(O)R^6$; $SO_2R^6$; $SONR^6R^7$; $SO_2NR^6R^7$; $OSO_2NR^6R^7$;

wherein $R^6$ and $R^7$ are independently of each other hydrogen; optionally substituted alkyl chain; optionally substituted alkenyl chain; optionally substituted alkynyl chain; optionally substituted heterocyclic or optionally substituted aryl;

each aryl as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy;

each heterocycle as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$ alkoxy$C_{1-6}$ alkyl, $C_{1-6}$alkylcarbonyl, amino, mono- or di$C_{1-6}$ alkylamino, azido, mercapto, polyhalo$C_{1-6}$ alkyl, polyhalo $C_{1-6}$alkoxy, and $C_{3-7}$ cycloalkyl, or a derivative of said compound of formula (I) having the formula:

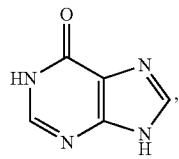

provided that the compound of formula (I) is not caffeine (represented by the following formula):

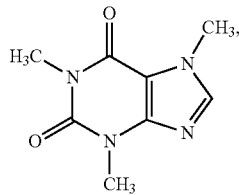

for use in the treatment of myotonic dystrophy type 1 and type 2.

Caffeine has been excluded and it has been object of the co-pending application EP14382450 because it has been observed that this particular compound acts through a different action mechanism and it was found suitable to explain how this compound acts in a different application.

One skilled in the art will readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

In addition, when a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and sub-combination possible of the group are intended to be individually included in the disclosure. When a compound is described herein such that a particular isomer, enantiomer, or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure.

The molecules disclosed herein may contain one or more ionisable groups (groups from which can be removed or added or which can be quaternized (e.g. amines)). All possible ionic forms of such molecules and salts thereof are intended to be included individually in the disclosure herein.

In a particular embodiment, said compound is in the form of a tautomer, solvate, hydrate, a pharmaceutically acceptable salt thereof or forming oligomers, preferably dimers.

In a preferred embodiment of the compound of formula (I), $R^1$, $R^2$, $R^3$ are independently each other H or Me, provided that this compound is not caffeine ($R^1=R^2=R^3=CH_3$).

In another preferred embodiment of the compound of formula (I), $R^3$ is a linker as defined above forming compounds as shown below:

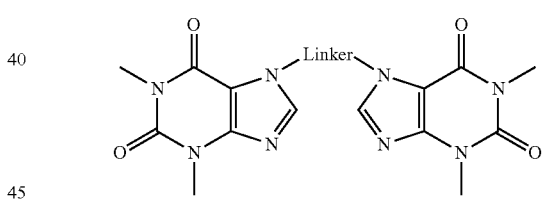

wherein the N to which the linker is bound is defined as N-7.

In another preferred embodiment, said compound is selected from the group consisting of theophylline, theobromine, aminophylline, xanthine, hypoxanthine, 1,7-dimethylxanthine, 3-isobutyl-1-methylxanthine, 3-methylxanthine, 3-ethyl-1-propylxanthine, 3-allyl-1-ethyl-8-hydroxyxanthine, 3,8-dimethyl-2-thioxanthine, 1-ethyl-3-isobutylxanthine,

A

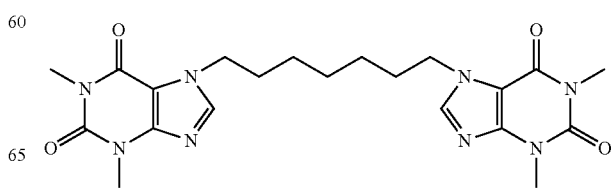

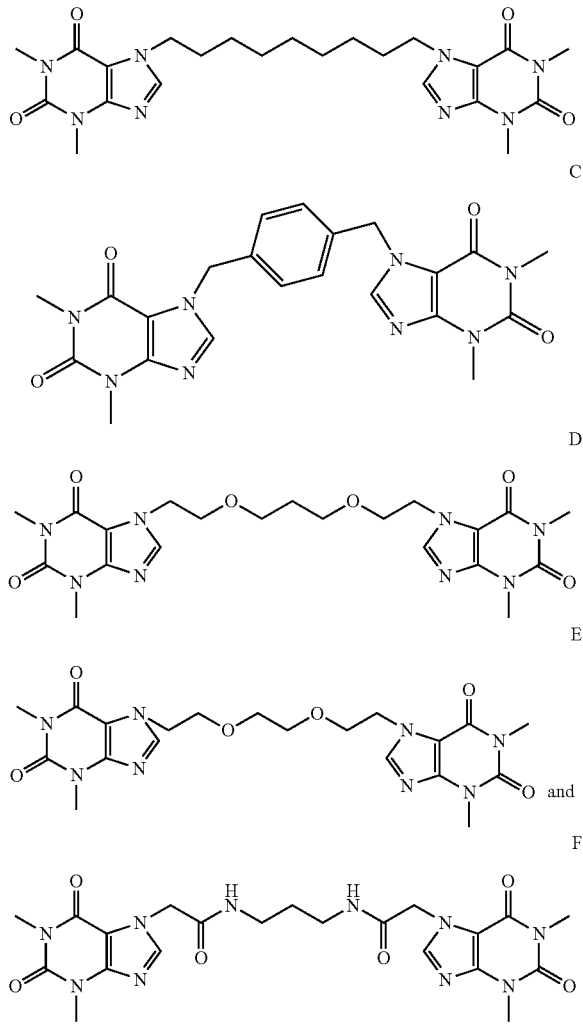

As used in the foregoing and hereinafter, the following definitions apply unless otherwise noted.

The term halo is generic to fluoro, chloro, bromo and iodo.

The term "oligomers" as used herein refers to complex molecules consisting of several monomeric units, for instance, dimers, trimers, tetramers, etc. Oligomers could be composed of homomonomers, when the two molecules are identical (e.g. A-A) or heteromonomers when they are not (e.g. A-B). Particularly preferred are dimers, consisting of two monomeric units joined by covalent bonds in the form of compound (I)-linker-compound (I), or by intermolecular or intramolecular interactions. Dimers joined by covalent bonding are preferably attached through their corresponding N-7.

The term "alkyl" as used herein it does refer to any linear, branched, or cyclic hydrocarbon in which all carbon-carbon bonds are single bonds.

The term "alkenyl" as used herein it does refer to any linear, branched, or cyclic alkyl with at least one carbon-carbon double bond.

Furthermore, the term "alkynyl" as used herein it does refer to any linear, branched, or cyclic alkyl or alkenyl with at least one carbon-carbon triple bond.

The term "cycloalkyl" refers to cyclic alkyl groups having a single cyclic ring or multiple condensed rings. The cycloalkyl can be unsubstituted or substituted. The cycloalkyl group can optionally include one or more cites of unsaturation.

The term "polyhalo$C_{1-6}$ alkyl" as a group or part of a group, e.g. in polyhalo$C_{1-6}$ alkoxy, is defined as mono- or polyhalo substituted $C_{1-6}$ alkyl, in particular $C_{1-6}$ alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$ alkyl groups, which are $C_{1-6}$ alkyl groups wherein all hydrogen atoms are replaced by fluorine atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$ alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$ alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$ alkyl is $C_{1-4}$ alkyl.

The term "$C_{2-6}$alkenyl" as a group or part of a group defines straight and branched chained hydrocarbon radicals having saturated carbon-carbon bonds and one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like.

$C_{3-7}$ cycloalkyl is generic to cyclopropyl, cyclobutyl, cyclopentyl, cyclohexyl and cycloheptyl.

$C_{1-6}$ alkoxy means $C_{1-6}$ alkyloxy wherein $C_{1-6}$ alkyl is as defined above.

The term "alkylcycloalkylalkyl" means an alkyl group substituted by an alkylcycloalkyl group. "Alkylcycloalkyl" means a cycloalkyl group substituted with at least one alkyl group.

The term "alkylcycloalkenylalkyl" means an alkyl group substituted by an alkylcycloalkenyl group. "Alkylcycloalkenyl" means a cycloalkyl group substituted with an at least one alkenyl group.

The term "alkylcycloalkylalkynyl" means an alkyl group substituted by an alkylcycloalkynyl group. "Alkylcycloalkynyl" means a cycloalkyl group substituted with an least one alkynyl group.

The term "alkylcycloalkenylalkyl" means an alkyl group substituted by an alkenylcycloalkyl group. "Alkylcycloalkenyl" means a cycloalkenyl group substituted with an least one alkyl group.

The term "alkylcycloalkenylalkyl" means an alkyl group substituted by an alkenylcycloalkyl group. "Alkylcycloalkenyl" means a cycloalkenyl group substituted with an least one alkyl group.

The term "alkylarylalkyl," as used herein, refers to an alkylaryl group attached to the parent molecular moiety through an alkyl group.

The term "alkylarylalkenyl" means an alkyl group substituted by an arylalkenyl group. "Arylalkenyl" means an aryl group with an alkenyl group.

The term "alkylarylalkynyl" means an alkyl group substituted by an arylalkynyl group. "Arylalkynyl" means an aryl group with an alkynyl group.

The term "alkylheterocycloalkyl," as used herein, refers to an alkylheterocycle group attached to the parent molecular moiety through an alkyl group. "Heterocycloalkyl" means an heterocycle group with an alkyl group.

The term "alkylheterocycloalkenyl," as used herein, refers to an alkylheterocycle group attached to the parent molecular moiety through an alkenyl group. "Heterocycloalkenyl" means an heterocycle group with an alkenyl group.

The term "alkylheterocycloalkynyl," as used herein, refers to an alkylheterocycle group attached to the parent molecular moiety through an alkenyl group. "Heterocycloalkynyl" means an heterocycle group with an alkenyl group.

The term "aryl" as used herein it does refer to any aromatic hydrocarbon group derived from the removal of at least one hydrogen atom from a single carbon atom of a parent aromatic ring system. The aryl group can have from 6 to 30 carbon atoms. The aryl group can have a single ring (e.g. phenyl) or multiple condensed (fused) rings, wherein at least one ring is aromatic. Typical aryl groups include, but are not limited to, radicals derived from benzene, naphthalene, anthracene, biphenyl, and the like. The aryl can be unsubstituted or optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$ alkylamino, azido, mercapto, polyhalo$C_{1-6}$alkyl, and polyhalo$C_{1-6}$alkoxy. The term "alkaryl" is employed where an aryl is covalently bound to an alkyl, alkenyl, or alkynyl.

The term "heteroaryl" refers to a monocyclic, bicyclic, or tricyclic ring systems containing one, two, or three aromatic rings and containing at least one nitrogen, oxygen, or sulfur atom in an aromatic ring. The heteroaryl can be unsubstituted or substituted, for example, with one or more substituents. A heterocycle group also can contain an oxo group (=O) or a thioxo (=S) group attached to the ring.

The term "heterocycle" refers to a saturated or partially unsaturated ring system, containing at least one heteroatom selected from the group oxygen, nitrogen, silicon, and sulfur, and optionally substituted with one or more groups as defined for the term "substituted".

The term "linker" refers to a cross-linking spacer that is used to attach two molecules to conform a dimer. Preferred linkers are selected from an optionally substituted alkyl, an optionally substituted alkenyl, an optionally substituted alkynyl, an optionally substituted cycloalkyl, an optionally substituted cycloalkenyl, an optionally substituted cycloalkynyl, an optionally substituted alkylcycloalkylalkyl, an optionally substituted alkylcycloalkylalkenyl, an optionally substituted alkylcycloalkylalkynyl, an optionally substituted alkylcycloalkenylalkyl, an optionally substituted alkylcycloalkynylalkyl, an optionally substituted aryl, an optionally substituted alkylarylalkyl, an optionally substituted alkylarylalkenyl, an optionally substituted alkylarylalkynyl, an optionally substituted heterocycle, an optionally substituted alkylheterocycloalkyl, an optionally substituted alkylheterocycloalkenyl, an optionally substituted alkylheterocycloalkynyl.

The term "substituted" as used herein refers to a replacement of an atom or chemical group (e.g., H, $NH_2$, or OH) with a functional group, the "substituent", and particularly contemplated substituents include nucleophilic groups. The substituent can be one of a selection of indicated groups, or it can be a suitable group known to those of skill in the art, provided that the substituted atoms' normal valency is not exceeded, ant that the substitution results in a stable compound. Suitable substituent groups include, but are not restricted to, polar groups (e.g., —$NH_2$, —OH, —SH, —NC, etc.), electrophilic groups (e.g., C(O)OR, C(X)OH, etc.), non-polar groups (e.g., aryl, alkyl, alkenyl, alkynyl, etc.), ionic groups (e.g., —$NH_3^+$), and halogens (e.g., —F, —Cl), and all chemically reasonable combinations thereof. Thus, the term "functional group" and the term "substituent" are used interchangeably herein and refer to nucleophilic groups (e.g., —$NH_2$, —OH, —SH, —NC, —CN, etc.), electrophilic groups (e.g., C(O)OR, C(X)OH, C(Halogen)OR, etc.), polar groups (e.g., —OH), non-polar groups (e.g., aryl, alkyl, alkenyl, alkynyl, etc.), ionic groups (e.g., —$NH_3^+$), and halogens.

It should be noted that the radical positions on any molecular moiety used in the definitions may be anywhere on such moiety as long as it is chemically stable.

Radicals used in the definitions of the variables include all possible positional isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), each and any of the subgroups thereof, N-oxides, addition salts, quaternary amines, metal complexes, and stereochemically isomeric forms.

The compounds of formula (I) may have one or more centers of chirality and may exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their N-oxides, salts, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Some of the compounds of formula (I) may also exist in their tautomeric form. Such forms although not explicitly indicated in the above formula are intended to be included within the scope of the present invention.

The term "tautomer" or "tautomeric form" refers to structural isomer of different energies which are interconvertible via a low energy barrier. For example, proton tautomers (also known as prototropic tautomers) include interconversion via migration of a proton, such as keto-enol and imine-enamine isomerizations. Valence tautomers include interconversions by reorganization of some of the bonding electrons.

The present disclosure also includes the prodrugs of compounds of formula (I).

The term "prodrug" as used throughout this text means the pharmacologically acceptable derivatives such as esters, amides, and phosphates, such that the resulting in vivo biotransformation product of the derivative is the active drug as defined in the compounds of formula (I). The reference by Goodman and Gilman (The Pharmacological Basis of Therapeutics, 8th ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolyzed in the human or animal body to produce the parent acid or alcohol. Suitable pharmaceutically acceptable esters for carboxy include $C_{1-6}$ alkoxymethyl esters for example methoxymethyl, $C_{1-6}$alkanoyloxymethyl esters for example pivaloyloxymethyl, phthalidyl esters, $C_{3-8}$ cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyl-oxyethyl which may be formed at any carboxy group in the compounds of this invention.

An in vivo hydrolysable ester of a compound of the formula (I) containing a hydroxy group includes inorganic esters such as phosphate esters and a-acyloxyalkyl ethers and related compounds which as a result of the in vivo hydrolysis of the ester breakdown to give the parent hydroxy group. Examples of a-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylamino acetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. "Pharmaceutically acceptable" as used herein means that the extract, fraction thereof, or compound thereof or composition is suitable for administration to a subject to achieve the treatments described herein, without unduly deleterious side effects in light of the severity of the disease and necessity of the treatment. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

The present invention also relates to a composition comprising at least one compound of formula (I)

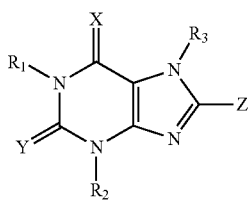

(I)

wherein:

$R^1$ is hydrogen; an optionally substituted alkyl chain, preferably optionally substituted methyl, more preferably methyl; an optionally substituted alkenyl; an optionally substituted alkynyl; an optionally substituted cycloalkyl; an optionally substituted cycloalkyl linked to N by an optionally substituted alkyl; an optionally substituted cycloalkyl linked to N by an optionally substituted alkenyl; an optionally substituted cycloalkyl linked to N by an optionally substituted alkynyl; an optionally substituted cycloalkenyl; an optionally substituted cycloalkenyl linked to N by an optionally substituted alkyl; an optionally substituted cycloalkenyl linked to N by an optionally substituted alkenyl; an optionally substituted cycloalkenyl linked to N by an optionally substituted alkynyl; an optionally substituted aryl; an optionally substituted aryl linked to N by an optionally substituted alkyl; an optionally substituted aryl linked to N by an optionally substituted alkenyl; an optionally substituted aryl linked to N by an optionally substituted alkynyl; an optionally substituted heterocycle; an optionally substituted heterocycle linked to N by an optionally substituted alkyl; an optionally substituted heterocycle linked to N by an optionally substituted alkyl; an optionally substituted heterocycle linked to N by an optionally substituted alkenyl; an optionally substituted heterocycle linked to N by an optionally substituted alkynyl chain; $COR^E$; $CONR^6R^7$; $CO_2R^6$; $CSR^6$; $C(S)OR^7$; $CSNR^6R^7$; $SO_2R^6$; CN;

$R^2$ is hydrogen; an optionally substituted alkyl chain, preferably optionally substituted methyl, more preferably methyl; an optionally substituted alkenyl; an optionally substituted alkynyl; an optionally substituted cycloalkyl; an optionally substituted cycloalkyl linked to N by an optionally substituted alkyl; an optionally substituted cycloalkyl linked to N by an optionally substituted alkenyl; an optionally substituted cycloalkyl linked to N by an optionally substituted alkynyl; an optionally substituted cycloalkenyl; an optionally substituted cycloalkenyl linked to N by an optionally substituted alkyl; an optionally substituted cycloalkenyl linked to N by an optionally substituted alkenyl; an optionally substituted cycloalkenyl linked to N by an optionally substituted alkynyl; an optionally substituted aryl; an optionally substituted aryl linked to N by an optionally substituted alkyl; an optionally substituted aryl linked to N by an optionally substituted alkenyl; an optionally substituted aryl linked to N by an optionally substituted alkynyl; an optionally substituted heterocycle; an optionally substituted heterocycle linked to N by an optionally substituted alkyl; an optionally substituted heterocycle linked to N by an optionally substituted alkenyl; an optionally substituted heterocycle linked to N by an optionally substituted alkynyl; $COR^6$; $CONR^6R^7$; $CO_2R^6$; $CSR^6$; $C(S)OR^7$; $CSNR^6R^7$; $SO_2R^6$; CN;

$R^3$ is hydrogen; an optionally substituted alkyl chain, preferably optionally substituted methyl, more preferably methyl; an optionally substituted alkenyl; an optionally substituted alkynyl; an optionally substituted cycloalkyl; an optionally substituted cycloalkyl linked to N by an optionally substituted alkyl; an optionally substituted cycloalkyl linked to N by an optionally substituted alkenyl; an optionally substituted cycloalkyl linked to N by an optionally substituted alkynyl; an optionally substituted cycloalkenyl; an optionally substituted cycloalkenyl linked to N by an optionally substituted alkyl; an optionally substituted cycloalkenyl linked to N by an optionally substituted alkenyl; an optionally substituted cycloalkenyl linked to N by an optionally substituted alkynyl; an optionally substituted aryl; an optionally substituted aryl linked to N by an optionally substituted alkyl; an optionally substituted aryl linked to N by an optionally substituted alkenyl; an optionally substituted aryl linked to N by an optionally substituted alkynyl; an optionally substituted heterocycle; an optionally substituted heterocycle linked to N by an optionally substituted alkyl; an optionally substituted heterocycle linked to N by an optionally substituted alkyl; an optionally substituted heterocycle linked to N by an optionally substituted alkenyl; an optionally substituted heterocycle linked to N by an optionally substituted alkynyl; $COR^6$; $CONR^6R^7$; $CO_2R^6$; $C(S)R^6$; $C(S)OR^6$; $CSNR^6R^7$; $S(O)R^6$; $SO_2R^6$; $SONR^6R^7$; $SO_2NR^6R^7$; a linker attached to another compound of formula (I) through N-7 (the one linked to $R^3$ in structure of formula (I)) wherein the linker is selected from an optionally substituted alkyl, an optionally substituted alkenyl, an optionally substituted alkynyl, an optionally substituted cycloalkyl, an optionally substituted cycloalkenyl, an optionally substituted cycloalkynyl, an optionally substituted alkylcycloalkylalkyl, an optionally substituted alkylcycloalkylalkenyl, an optionally substituted alkylcycloalkylalkynyl, an optionally substituted alkylcycloalkenylalkyl, an optionally substituted alkylcycloalkynylalkyl, an optionally substituted aryl, an optionally substituted alkylarylalkyl, an optionally substituted alkylarylalkenyl, an optionally substituted alkylarylalkynyl, an optionally substituted heterocycle, an optionally substituted alkylheterocycloalkyl, an optionally substituted alkylheterocycloalkenyl, an optionally substituted alkylheterocycloalkynyl;

X is O, NH, S;

Y is O, NH, S independently of X;

Z is hydrogen; an optionally substituted alkyl chain, preferably optionally substituted methyl, more preferably methyl; an optionally substituted alkenyl chain; an optionally substituted alkynyl chain; an optionally substituted cycloalkyl; an optionally substituted cycloalkyl linked through an optionally substituted alkyl; an optionally substituted cycloalkyl linked through an optionally substituted alkenyl; an optionally substituted cycloalkyl linked through an optionally substituted alkynyl chain; an optionally substituted cycloalkenyl; an optionally substituted cycloalkenyl linked through an optionally substituted alkyl; an optionally substituted cycloalkenyl linked through an optionally substituted alkenyl; an optionally substituted cycloalkenyl linked through an optionally substituted alkynyl chain; an optionally substituted aryl; an optionally substituted aryl linked through an optionally substituted alkyl; an optionally substituted aryl linked through an optionally substituted alkenyl; an optionally substituted aryl linked through an optionally substituted alkynyl chain; an optionally substituted heterocycle; an optionally substituted heterocycle linked through an optionally substituted alkyl; an optionally substituted heterocycle linked through an optionally substituted alkyl; an optionally substituted heterocycle linked through an optionally substituted alkenyl; an optionally substituted heterocycle linked through an optionally substituted alkynyl chain; OH; SH; $NH_2$; halogen; $OR^6$; $SR^6$; $NR^6R^7$; CN; $N_3$; $COR^6$; $CONR^6R^7$; $CO_2R^6$; $C(S)R^6$; $C(S)OR^6$; $CSNR^6R^7$; $OCONR^6R^7$; $OCO_2R^6$; $OC(S)R^6$; $OC(S)OR^6$; $NHCONR^6R^7$; $NHCOR^6$; $NHCO_2R^6$; $NHC(S)OR^6$; $S(O)R^6$; $SO_2R^6$; $SONR^6R^7$; $SO_2NR^6R^7$; $OSO_2NR^6R^7$; wherein $R^6$ and $R^7$ are independently of each other hydrogen; optionally substituted alkyl chain; optionally substituted alkenyl chain; optionally substituted alkynyl chain; optionally substituted heterocyclic or optionally substituted aryl;

each aryl as a group or part of a group is phenyl or naphthalenyl, each optionally substituted with one, two or three substituents selected from halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, and polyhalo$C_{1-6}$alkoxy;

each heterocycle as a group or part of a group is a monocyclic ring with 5 or 6 ring atoms or a bicyclic ring structure comprising a 6 membered ring fused to a 4, 5, or 6 membered ring; each of the rings being saturated, partially unsaturated, or completely unsaturated; at least one of the rings containing 1 to 4 heteroatoms each independently selected from nitrogen, oxygen and sulphur; and any one of the rings being optionally substituted with one, two or three substituents each independently selected from the group consisting of halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, amino, mono- or di$C_{1-6}$alkylamino, azido, mercapto, polyhalo$C_{1-6}$alkyl, polyhalo$C_{1-6}$alkoxy, and $C_{3-7}$cycloalkyl, or a derivative of said compound of formula (I) having the formula:

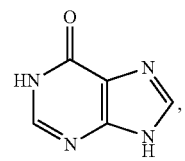

provided that the compound of formula (I) is not caffeine (represented by the following formula):

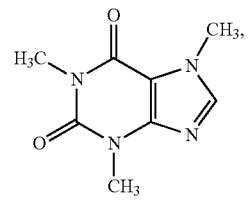

for use in the treatment of myotonic dystrophy type 1 and type 2.

In a particular embodiment of said composition, the compound of formula (I) comprised in the composition is in the form of a tautomer, solvate, hydrate, a pharmaceutically acceptable salt thereof or forming oligomers as defined above.

In another particular embodiment of said composition, in the compound of formula (I) comprised in the composition $R^1$, $R^2$, $R^3$ are independently each other H or Me, provided that this compound is not caffeine ($R^1$=$R^2$=$R^3$=$CH_3$).

In another particular embodiment of said composition, in the compound of formula (I) comprised in the composition, $R^3$ is a linker as defined above forming compounds as shown below:

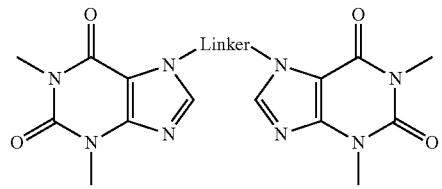

wherein the N to which the linker is bound is defined as N-7.

In a preferred embodiment, said composition comprises caffeine.

The present invention also relates to a method of treatment of myotonic dystrophy type I in a subject comprising administering to said subject a therapeutically effective amount of the compound of formula (I) or a tautomer, solvate, hydrate, a pharmaceutically acceptable salt thereof or forming oligomers as defined above. Preferably the subject is a human subject. In addition, the present invention also relates to a method of treatment of myotonic dystrophy type I in a subject comprising administering to said subject a therapeutically effective amount of a composition comprising a compound of formula (I) or a tautomer, solvate, hydrate, a pharmaceutically acceptable salt thereof or forming oligomers as defined above. The phrase "therapeutically effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present disclosure may be administered in a sufficient amount to produce a reasonable benefit/risk ratio applicable to such treatment.

As used herein, a patient or subject who will suffer from myotonic dystrophy type 1 or 2 is defined as a person who carried any of the gene mutations disclosed in the background section, even though the disease has not developed.

In a preferred embodiment of said composition, the compound of formula (I) is selected from the group consisting of theophylline, theobromine, aminophylline, xanthine, hypoxanthine, 1,7-dimethylxanthine, 3-isobutyl-1-methylxanthine, 3-methylxanthine, 3-ethyl-1-propylxanthine, 3-allyl-1-ethyl-8-hydroxyxanthine, 3,8-dimethyl-2-thioxanthine, 1-ethyl-3-isobutylxanthine,

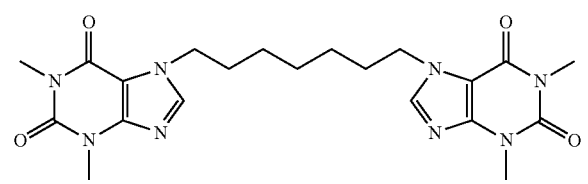

A

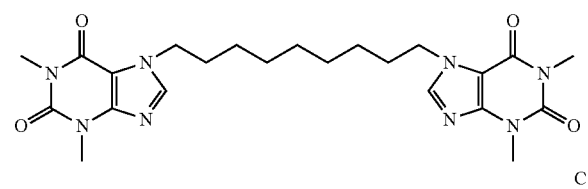

B

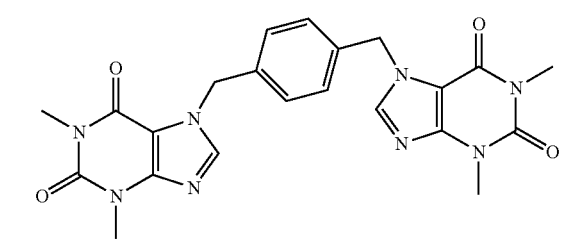

C

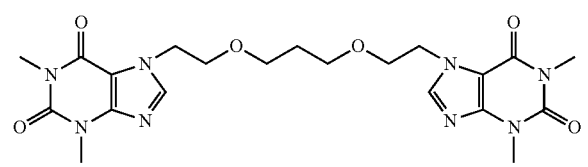

D

-continued

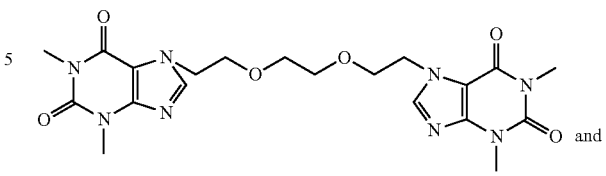

E and

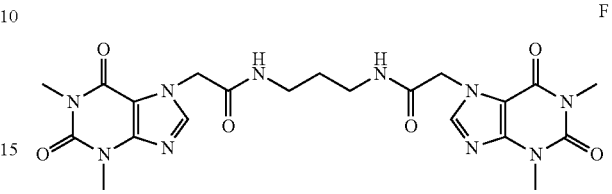

F

In another preferred embodiment, the composition for use according to the present invention is formulated as a pharmaceutical composition, food, food ingredient or supplement, nutraceutical composition, additive for a natural product or is present in the extract of a natural product. Preferably, said composition is the form of a solid or liquid. More preferably, said composition is present in a dairy product, a beverage, a chocolate product, or cereals. Even more preferably, said composition is present in a food supplement or a nutraceutical composition A composition of a "food" item or "food ingredient or supplement" as described above may in principle take any form suited for consumption by man or animal. In one embodiment the composition is in the form of a dry powder that can be suspended, dispersed, emulsified or dissolved in an aqueous liquid such as water, coffee, tea, milk, yogurt, stock or fruit juice and alcoholic drinks. To this end, the powder may be provided in unit-dosage form. In an alternative preferred embodiment the composition in the form of a dry powder is tabletted. To that end, a composition for a food supplement according to the invention may very suitably be provided with fillers, such as microcrystalline cellulose (MCC) and mannitol, binders such as hydroxypropylcellulose (HPC), and lubricants such as stearic acid or other excipients. A composition of a food item or food supplement as described above may also be provided in the form of a liquid preparation wherein the solids are suspended, dispersed or emulsified in an aqueous liquid. Such a composition may be admixed directly through a food item or may e.g. be extruded and processed to grains or other shapes. In an alternative embodiment a food item or food supplement may take the shape of a solid, semi-solid or liquid food item, such as cereals, a bread, a bar, a cookie, a sandwich or a beverage, or as a spread, sauce, butter, margarine, dairy product, and the like. Preferably, the composition is included in a dairy product, such as for instance a butter or margarine, custard, yogurt, cheese, spread, drink, or pudding or other dessert.

Nutraceuticals can be defined as natural products that are used to supplement the diet by increasing the total dietary intake of important nutrients. This definition includes nutritional supplements such as vitamins, minerals, herbal extracts, antioxidants, amino acids, and protein supplements. Nutraceutical products fit into the newly created product category of "Dietary Supplements" as established by the F.D.A. in the Dietary Supplement Act of 1994. This act specifically defined dietary supplements to include: vitamins, minerals, herbs or other botanicals, antioxidants, amino acids, or other dietary substances used to supplement the diet by increasing the total daily intake. A "nutraceutical composition" is defined herein as a food composition fortified with ingredients capable of producing health benefits. Such a composition in the context of the present invention may also be indicated as foods for special dietary use; medical foods; and dietary supplements. For example, the food item or supplement may help to prevent or reduce symptoms associated with an inflammatory condition such as allergies (e.g. hay fever) and the like. As with the pharmaceutical composition, the amount of active ingredient in the food or food additive will depend on several factors. The food product will generally comprise a concentration that is sufficient to provide a consumer with an effective amount of active ingredient upon consumption of a regular (e.g. daily) portion of the food product. It will be recognized by those skilled in the art that the optimal quantity and spacing of individual dosages for achieving the therapeutic effects of the pharmaceutical composition, food item or food supplement described herein may easily be determined by the skilled person.

As mentioned above, the compounds or compositions disclosed herein can also be present in natural products. For example, it is well known that several natural herbs contain methylxanthines (theophylline, theobromine). Accordingly, it can be possible to use a extract of the natural product containing the active ingredient (compound of formula (I)) for the purposes of the present invention. The compound of formula (I) can even be used as an additive for natural products for enhancing the intrinsic effect of the compounds of formula (I) already found in the natural product.

In another preferred embodiment, the compound or composition disclosed herein is administered by oral, rectal, nasal, topical, vaginal, parenteral, transdermal, intraperitoneal, intrapulmonary and intranasal route.

In another preferred embodiment, the compound or composition disclosed herein is administered to a patient having a non-congenital form of DM.

Dose ranges of the pharmaceutical compositions can be adjusted as necessary for the treatment of individual patients and according to the specific condition treated. Any of a number of suitable pharmaceutical formulations may be utilized as a vehicle for the administration of the compositions of the present invention and maybe a variety of administration routes are available. The particular mode selected will depend of course, upon the particular formulation selected, the severity of the disease, disorder, or condition being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes and the like. Accordingly, the formulations of the invention include those suitable for oral, rectal, topical, buccal, sublingual, parenteral (e.g., subcutaneous, intramuscular, intradermal, inhalational or intravenous) and transdermal administration, although the most suitable route in any given case will depend on the nature and severity of the condition being treated and on the nature of the particular active product used.

Formulations suitable for oral administration may be presented in discrete units, such as capsules, cachets, lozenges, drops, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, inhalational or intradermal injection. Such preparations may conveniently be prepared by admixing the compound with water or a glycine buffer and rendering the resulting solution sterile and isotonic with the blood.

Formulations of the inventive mixtures are particularly suitable for topical application to the skin and preferably take the form of an ointment, cream, lotion, paste, gel, spray, aerosol, or oil. Carriers which may be used include Vaseline, lanoline, polyethylene glycols, alcohols, transdermal enhancers, and combinations of two or more thereof.

Formulations suitable for transdermal administration may also be presented as medicated bandages or discrete patches adapted to remain in intimate contact with the epidermis of the recipient for a prolonged period of time. Formulations suitable for transdermal administration may also be delivered by iontophoresis (passage of a small electric current to "inject" electrically charged ions into the skin; also called electromotive drug administration (EMDA)) through the skin.

The present invention also relates to new compounds which are dimers of the compounds of formula (I), optionally in the form of a tautomer, solvate, hydrate or a pharmaceutically acceptable salt thereof as defined above. These compounds are represented by the following formula:

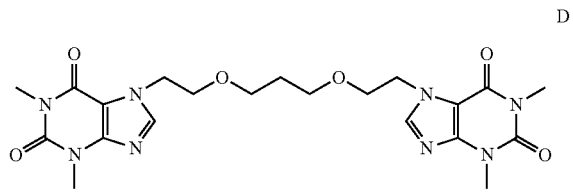

D

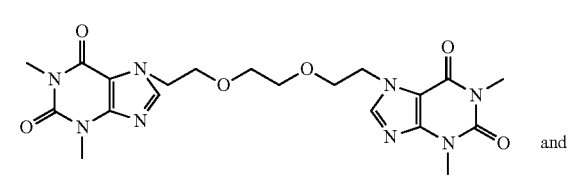

E and

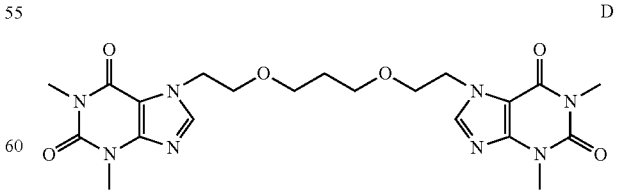
F

The process for obtaining these compounds is disclosed in the example section below. The present invention is now further illustrated by reference to the following examples.

EXAMPLES

Example 1

Preparation of compound A (Theophyilline-C7):
7,7'-(heptane-1,7-diyl)bis(1,3-dimethyl-1H-purine-2,6(3H,7H)-dione, CAS nr [156234-12-7])

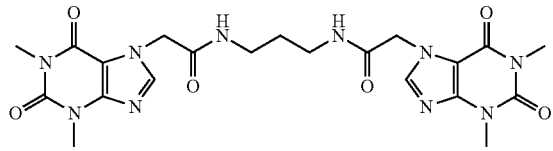
A

Under inert atmosphere, to a stirred solution of NaH (62 mg, 1.55 mmol) in 1 ml anhydrous DMF at 0° C., it was added a solution of theophylline (140 mg, 0.775 mmol) in 3 ml anhydrous DMF. After 1 h at 0° C., 1,7-dibromoheptane (65 μl, 0.388 mmol) was added to the reaction mixture. This mixture was stirred at room temperature overnight and an extra hour at 65° C., and then solvent was completely removed. The crude was chromatographically purified over $SiO_2$ using gradient mixtures of Hexane/AcOEt and AcOEt/MeOH as the eluant, yielding 0.070 g (40%) of the desired product A.

$^1$H NMR (400 MHz, DMSO-$d_6$): δ 8.06 (s, 2 H), 4.22 (t, J=7.0 Hz, 4 H), 3.42 (s, 6 H), 3.22 (s, 6 H), 1.75 (br. s., 4 H), 1.22 (br. s., 6 H) ppm.

MS (ESI (+)): m/z=479.2 [M+Na]$^+$
MS (ESI (−)): m/z=455.0 [M-H]$^-$

Example 2

Preparation of compound B (Theophyilline-C9):
7,7'-(nonane-1,9-diyl)bis(1,3-dimethyl-1H-purine-2,6(3H,7H)-dione, CAS nr [156234-13-8])

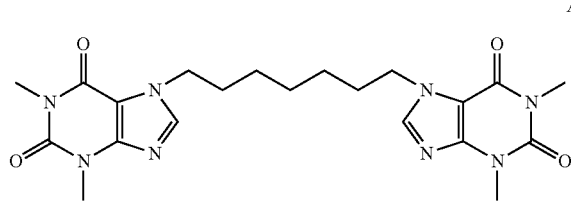
B

Under inert atmosphere, to a stirred solution of NaH (140 mg, 3.45 mmol) in 2 ml anhydrous DMF at 0° C., it was added a solution of theophylline (378 mg, 2.098 mmol) in 10 ml anhydrous DMF. After 2 h at room temperature, 1,9-dibromononane (142 μl, 1.41 mmol) was slowly added to the reaction mixture. This mixture was stirred at room temperature overnight, and then solvent was completely removed. The crude was chromatographically purified over $SiO_2$ using gradient mixtures of AcOEt/MeOH as the eluant, yielding 0.108 g (32%) of the desired product B.

$^1$H NMR (400 MHz, DMSO-$d_6$): δ 8.07 (s, 2 H), 4.22 (t, J=7.0 Hz, 1 H), 3.42 (s, 6 H), 3.22 (s, 6 H), 1.69-1.83 (m, 4H), 1.24 (br. s., 10H) ppm.

MS (ESI (+)): m/z=507.2 [M+Na]$^+$
MS (ESI (−)): m/z=483.0 [M-H]$^-$

Example 3

Preparation of compound C (Theophyilline-Bz):
7,7'-(1,4-phenylenebis(methylene))bis(1,3-dimethyl-1H-purine-2,6(3H,7H)-dione, CAS nr [865099-82-7])

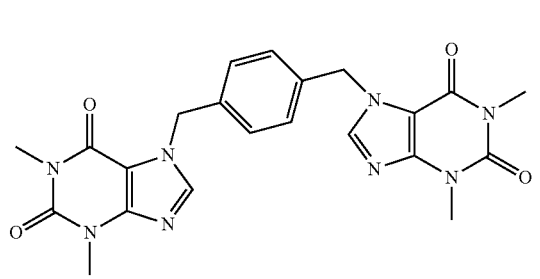
C

Under inert atmosphere, to a stirred solution of NaH (152 mg, 3.788 mmol) in 2 ml anhydrous DMF at 0° C., it was added a solution of theophylline (410 mg, 2.273 mmol) in 10 ml anhydrous DMF. After 2 h at room temperature, p-xylylene dibromide (200 mg, 0.758 mmol) was slowly added to the reaction mixture. This mixture was stirred at room temperature overnight, and then solvent was completely removed. The crude was chromatographically purified over $SiO_2$ using gradient mixtures of AcOEt/MeOH as the eluant, yielding the desired product C.

MS (ESI (+)): m/z=485.2 [M+Na]$^+$

Example 4

Preparation of compound D (Theophylline-PG):
7,7'-((propane-1,3-diylbis(oxy))bis(ethane-2,1-diyl))bis(1,3-dimethyl-1H-purine-2,6(3H,7H)-dione)

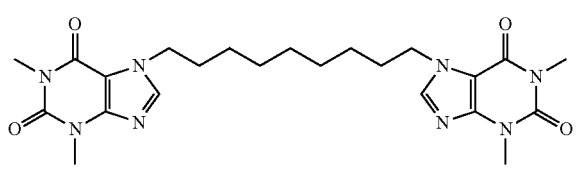
D

Step 1: To a stirred solution of 3,7-dioxa-1,9-nonandiol (0.25 g, 1.523 mmol) in anhydrous $CH_2Cl_2$ at 0° C., it was added 0.63 ml of anhydrous $Et_3N$ (4.57 mmol, 3 eq). To this solution, MsCl (3.65 mmol, 2.4 eq) was added and the mixture was stirred for at least 2 h at 0° C. Then, the crude was evaporated to dryness, and chromatographically purified, yielding 316 mg (65%) of the desired intermediate (propane-1,3-diylbis(oxy))bis(ethane-2,1-diyl) dimethanesulfonate.

Step 2: Under inert atmosphere, to a stirred solution of NaH (197 mg, 4.933 mmol) in anhydrous DMF at 0° C., it was added a solution of theophylline (533 mg, 2.96 mmol) in ml anhydrous DMF. After 1 h at room temperature, (propane-1,3-diylbis(oxy))bis(ethane-2,1-diyl) dimethanesulfonate from step 1 (316 mg, 0.987 mmol) was added to the reaction mixture. This mixture was stirred at room temperature overnight, and then at 50° C. during at least 24 h. The suspension is filtered, and the remaining solid was washed with NaOH 1N and AcOEt. After filtering, the recovered solid is identified as the desired product D.

MS (ESI (+)): m/z=511.1 [M+Na]$^+$

Example 5

Preparation of compound E (Theophyilline-EG): 7,7'-((ethane-1,2-diylbis(oxy))bis(ethane-2,1-diyl))bis(1,3-dimethyl-1H-purine-2,6(3H,7H)-dione)

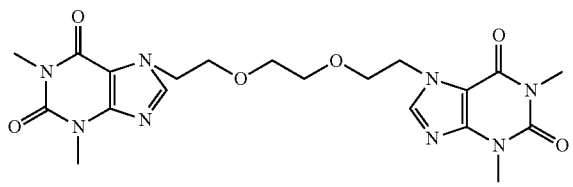

E

Under inert atmosphere, to a stirred solution of NaH (267 mg, 6.682 mmol) in anhydrous DMF at 0° C., it was added a solution of theophylline (722 mg, 4.01 mmol) in 27 ml anhydrous DMF. After 1 h at room temperature, 1,2-Bis(2-chloroethoxy)ethane (250 mg, 1.336 mmol) was added to the reaction mixture. This mixture was stirred at room temperature overnight, and then at 50° C. during at least 4 days. The suspension is filtered, and the remaining solid was washed with NaOH 1N and AcOEt, yielding 0.188 g (30%) of the desired product E.

MS (ESI (+)): m/z=497.0 [M+Na]$^+$

Example 6

Preparation of compound F (Theophyilline-AM): N,N'-(propane-1,3-diyl)bis(2-(1,3-dimethyl-2,6-dioxo-2,3-dihydro-1H-purin-7(6H)-yl)acetamide)

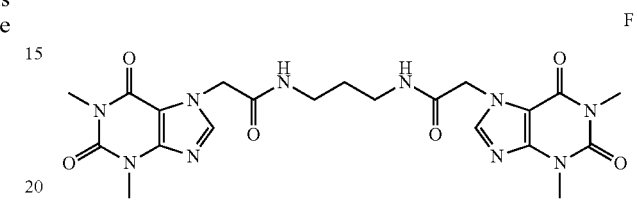

F

Step 1: Under inert atmosphere, 1,3-diaminopropane (0.25 g, 3.373 mmol) is added to to a stirred solution of pyridine (0.587 g, 7.42 mmol) in anhydrous acetonitrile (3 ml) at room temperature. Then, 0.60 ml of chloroacetyl chloride (0.838 mmol, 7.42 mmol) was slowly added at 0° C. The mixture was stirred for at least 2 h. Then, the crude was evaporated to dryness, and extracted with AcOEt, yielding 440 mg (57%) of the desired intermediate N,N'-(propane-1,3-diyl)bis(2-chloroacetamide).

Step 2: Under inert atmosphere, to a stirred solution of NaH (248 mg, 6.20 mmol) in anhydrous DMF at 0° C., it was added a solution of theophylline (1.05 g, 5.813 mmol) in anhydrous DMF. After 2 h at room temperature, N,N'-(propane-1,3-diyl)bis(2-chloroacetamide) from step 1 (440 mg, 1.938 mmol) was added to the reaction mixture. This mixture was stirred at room temperature overnight, and then at 50° C. during at least 4 h. After solvent evaporation, the remaining solid was washed with NaOH 1N and AcOEt, yielding 542 mg (54%) of the desired product F.

MS (ESI (+)): m/z=537.1 [M+Na]$^+$

TABLE 1

| Compound ID | Name | $R_1$ | $R_2$ | $R_3$ | X | Y | Z | CAS nr |
|---|---|---|---|---|---|---|---|---|
| 1 | Theophylline | Me | Me | H | O | O | H | [58-55-9] |
| 2 | Theobromine | H | Me | $CH_3$ | O | O | H | [83-67-0] |
| 3 | Aminophylline (=(Theophylline)$_2$•Ethylenediamine)) | Me | Me | H | O | O | H | [317-34-0] |
| 4 | Xanthine | H | H | H | O | O | H | [69-89-6] |
| 5 | Hypoxanthine | | | | | | | [68-94-0] |
| 6 | 1,7-Dimethylxanthine | Me | H | $CH_3$ | O | O | H | [611-59-6] |
| 7 | 3-Isobutyl-1-methylxanthine | Me | $^i$Bu | H | O | O | H | [28822-58-4] |
| 8 | 3-Methylxanthine | H | Me | H | O | O | H | [1076-22-8] |
| 9 | 3-Ethyl-1-propylxanthine | Pr | Et | H | O | O | H | [135462-23-6] |
| 10 | 3-Allyl-1-ethyl-8-hydroxyxanthine | Et | Allyl | H | O | O | OH | [194802-32-9] |
| 11 | 3,8-Dimethyl-2-thioxanthine | H | Me | Me | O | S | Me | [91725-06-3] |
| 12 | 1-Ethyl-3-isobutylxanthine | Et | $^i$Bu | H | O | O | H | [96654-24-9] |

TABLE 2

| Compound ID | Name | R₁ | R₂ | R₃ | X | Y | Correspondence to dimer |
|---|---|---|---|---|---|---|---|
| 17 | Theophylline-C7 | Me | Me | H | O | O | A |
| 18 | Theophylline-C9 | Me | Me | H | O | O | B |
| 19 | Theophylline-PG | Me | Me | H | O | O | D |
| 20 | Theophylline-EG | Me | Me | H | O | O | E |
| 21 | Theophylline-AM | Me | Me | H | O | O | F |

Xanthines Bind to CUG Repeats.

This was assessed in fluorescence polarization spectroscopy experiments. In these tests, when polarized light excites a fluorophore conjugated to a small molecule, it undergoes rotational diffusion faster than the time required for light emission occurs, resulting in a random arrangement of the molecule in the fluorescence emission time (depolarization). However, the rotation of the molecule becomes slower depending on the viscosity of the medium or the molecular volume, increasing the polarization of the emitted light. Thus, by measuring changes in polarization of an RNA with 23 CUG repeats conjugated to the fluorophore carboxyfluorescein, FAM (CUG) 23, we can consider whether a candidate molecule binds to the RNA. In this test we used as a positive control, pentamidine (Warf et al. 2009), a compound previously shown to be attached to the CUG repeats, and as negative control a pretesting compound know to be unable to bind CUGs.

Fluorescent CUG RNA (carboxyfluorescein (6-FAM)-labeled) was incubated with increasing concentrations of example compounds. Whereas 6-FAM-CUG RNA molecules do not fluorescence in any particular polarization axis, binding to a molecule slows down the rotational movement of the molecule and increases polarization values. By binding to CUG RNA, compounds have the ability to modify the toxicity of CUG repeats by a number of mechanisms including altering the conformation of the secondary structures that these RNAs have in solution or competitively inhibiting the sequestration of MBNL proteins.

For a given compound, polarization is sensitive to concentration.

Figure 2:
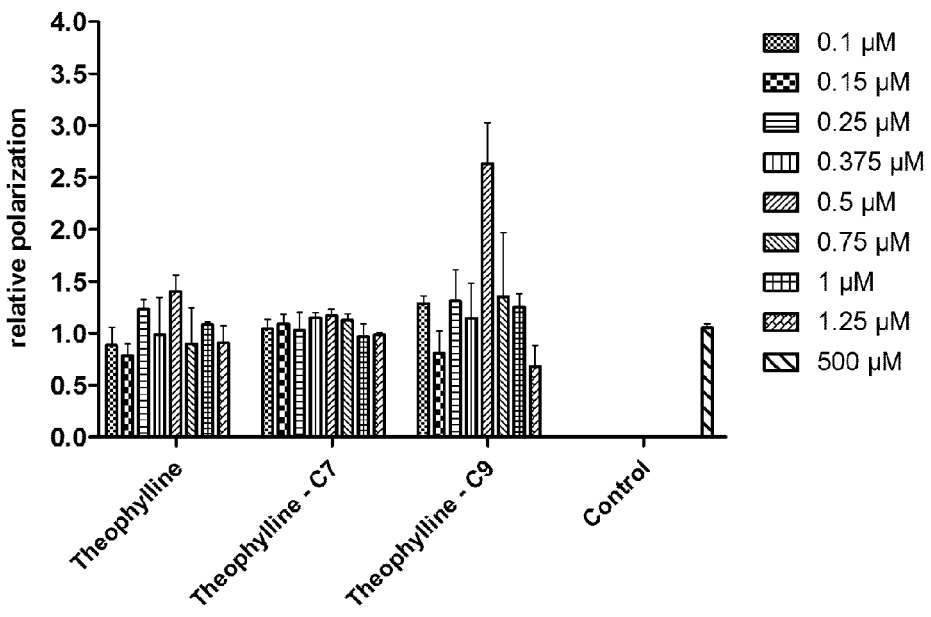
FIG. 2. Polarization measurements of the 6-FAM-(CUG) 23 probe in the presence of the indicated compounds is represented relative to the readings with the probe alone. Each of the compounds on the x-axis was tested at increasing concentrations. Higher polarization values indicate greater binding capacity to the CUG repeats. In comparison to a control compound that does not bind CUG repeats, the theophylline molecules exhibits a bond to CUG repeats which can range from a weak bond to a very strong bond in the case in which a nine carbon alkyl linker (C9) is present. Bar graph shows results from three independent experiments with four technical replicates each. Error bars are s.e.m.

See FIG. 1 and FIG. 2.

Materials and Methods
Polarization Fluorescence Assays:

Carboxyfluorescein-labeled CUG RNA (6-FAM-CUG$_{23}$) at 6 nM was incubated with the compounds at different concentrations in binding buffer (50 mM Tris-HCl pH 7.0, 250 mM NaCl, 50 µM ZnCl$_2$, 10% glycerol, 1 mM DTT) on ice for 20 min in the dark. Polarization was measured in an EnVision® Multilabel Reader using as excitation filter FP480 and as emission filter FP535.

Xanthines are not Toxic for Cells

To assess the toxicity of compounds in culture cells, different concentrations of compounds (from 0.1 to 100 microM) were added to standard media in DM1 fibroblasts and studied survival using the CellTiter 96 Aqueous Non-Radioactive cell proliferation assay protocol; colorimetric assay that determines viable cells.

As the percentage of survival was always above 50% in comparison to non-treated cells and above 75% in comparison to DMSO treated cells, all the concentrations were continued being used in the following assays of activity, as their toxicity was very low.

Figure 3:
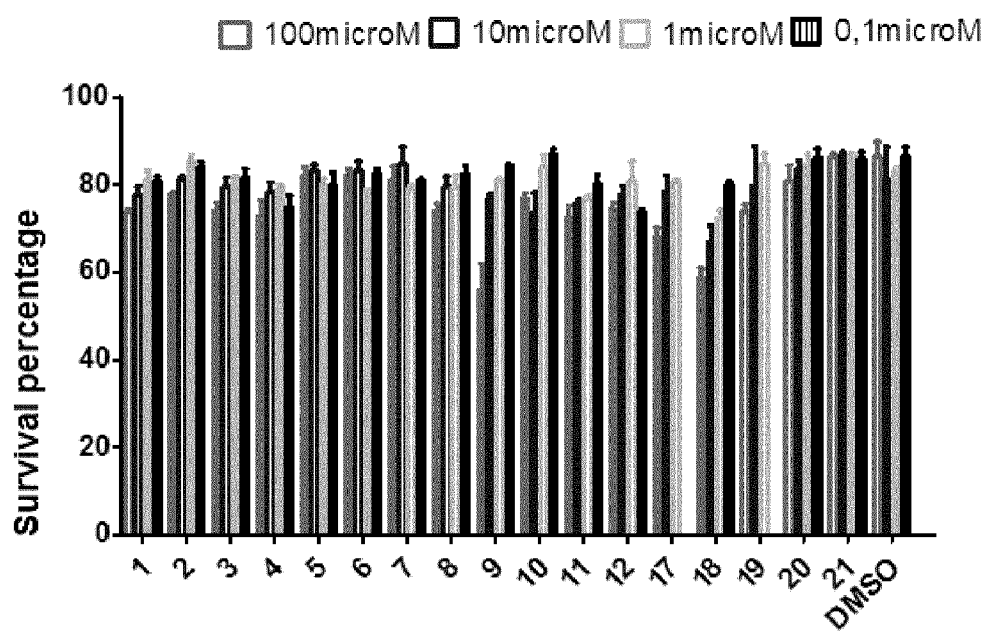
FIG. 3. Percentage of survival of DM1 fibroblasts after administration of different concentrations of compounds in the media. The values of survival are normalized to non-treated DM1 fibroblasts which have 100% of survival. In all cases, the compounds were dissolved in DMSO, then the cells treated only with DMSO are considered the most appropriate controls for comparison. Bar graph shows means+s.e.m. from three independent experiments.

See FIG. 3
Xanthines Reduce the Number of Ribonuclear Foci Per Cell

Its reduction is typically used as evidence of desired activity against myotonic dystrophy in cell culture models because MBNL proteins are sequestered in ribonuclear foci. Since MBNL proteins are limiting in myotonic dystrophies an increase in free MBNLs is expected to be therapeutic.

Figure 4:
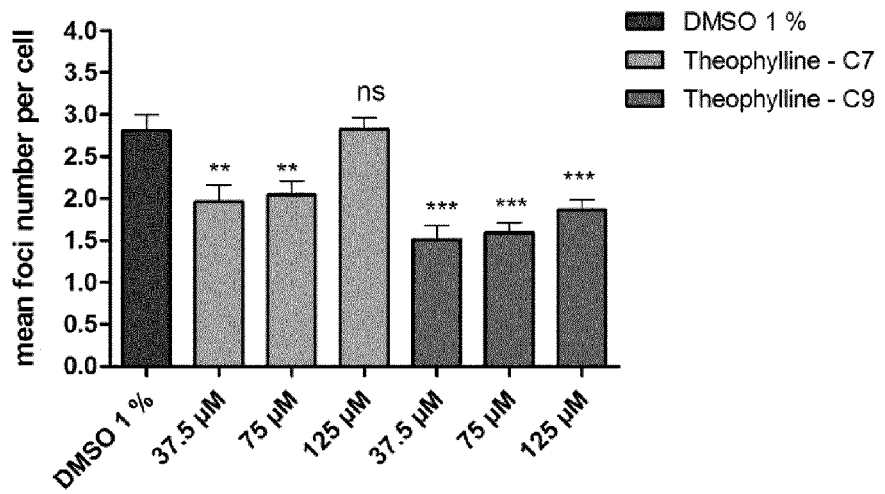
FIG. 4. Mean number of ribonuclear foci per cell in DM1 fibroblasts exposed to the indicated concentrations of compounds in the culture media. Theophylline-C7 and theophylline-C9 both significantly decreased the number of foci per cell.  Indicates p-value<0.001, * indicates p-value<0.0001. Data comes from three independent experiments with three technical replicates each. DMSO bar shows reference value for DM1 fibroblasts exposed to dilutent only. Error bars are s.e.m.

Evidences from Human Myoblasts:
See FIG. 4
Materials and Methods
Cell Culture Conditions Cell model of the disease (provided by the D. Furling's laboratory, Institute of Myologie, Paris) consisted of normal and DM1 (1300 CTG repeats) immortalized (hTERT) skin fibroblasts expressing conditional MyoD. Fibroblast cells were grown in Dulbecco's Modified Eagle Medium (DMEM) with 4.5 g/L of glucose, 1% of penicillin and streptomycin (P/S) and 10% foetal bovine serum (FBS) (Sigma). Fibroblasts were transdifferentiated in myoblasts by inducing expression of MyoD. Cells were plated in muscle differentiation medium (MDM) made of DMEM 4.5 g/L glucose with 1% P/S, 2% horse serum, 1% apo-transferrin (10 mg/ml), 0.1% insulin (10 mg/ml) and 0.02% doxycyclin (10 mg/ml) for 48 h. For compound testing fibroblasts were aliquoted in 24-well plate with 3.5×10⁴ cells per well and were differentiated as before. Compounds were added to a final concentration of 37.5 µM, 75 µM and 125 µM in MDM medium and cells were incubated for 48 h.

Foci Detection

In situ hybridization with CUG repeat RNA. Cells were fixed in 4% paraformaldehyde (PFA) for 10 min at room temperature followed by several washes in PBS 1×. Fixed cells were incubated in pre-hybridization buffer (SSC 2×, 30% deionized formamide) for 10 min at room temperature, hybridized with Cy3-(CAG)$_7$-Cy3 labelled probe diluted 1:100 in hybridization buffer (40% formamide, 2×SSC, 0.2% BSA, 10% dextran sulfate, 2 mM vanadyl complex, 10% tRNA (10 mg/ml), 10% herring sperm) for 2 h at 37° C., washed twice in pre-hybridization buffer for 15 min at 45° C., washed in PBS 1× for 15 min at room temperature and mounted in Vectashield (Vector) with 2 µg/ml DAPI. Images were taken using a Leica DM2500 fluorescence microscope and foci were manually counted from at least 50 cells per compound.

Xanthines Increase Muscleblind Protein
Quantification of Mbl Expression or Localization Immortalized transdifferentiated DM1 fibroblasts were seeded in a 94-well plate (8000 cell/per well) in standard media. To achieve the differentiation of the fibroblast to myoblasts, we induced MyoD expression by changing the standard media to differentiation media with Doxocycline and without serum. 24 h after induction, the compounds were added the cells at different concentrations, always maintaining the concentration of the solvent (DMSO) at 1% in the media. Every concentration of compound was tested in three different wells. 24 h after adding the compounds the cells were fixed with paraformaldehyde 4% in PBS and Mbl detection using monoclonal anti-MBNL1 antibody was performed counterstaining with Hoechst to detect the nuclei. Incell 200 plate reader confocal was used for detection and quantification of the parameters selected and the data was analyzed using Graphpad software for statistical comparison of results.

Figure 6:
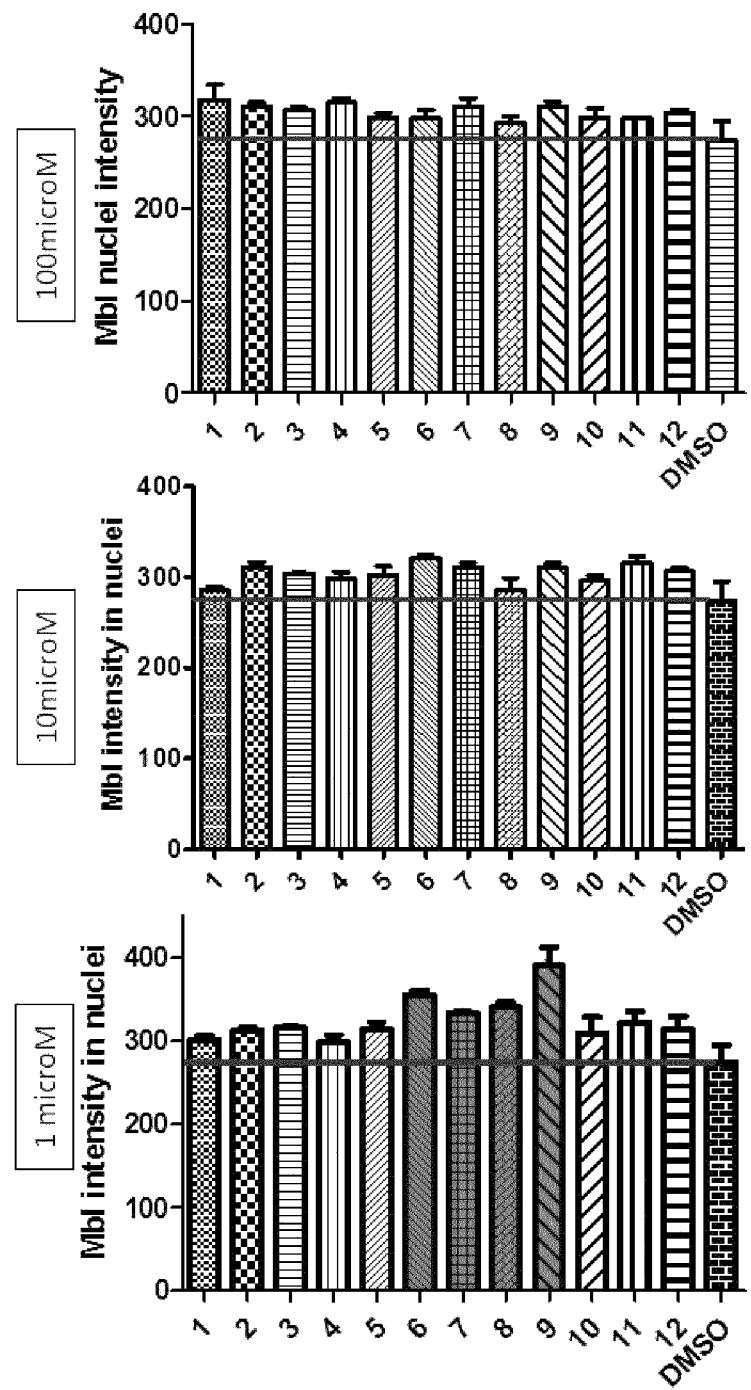
FIG. 6. Quantification of Mbl expression intensity in nuclei. Bar graphs show the mean±SEM of Mbl staining intensity in nuclei in DM1 myoblasts that had been treated with different concentrations of compounds (from 1 microM to 100 microM) or solvent (DMSO) during one day. Horizontal red line marks the reference value of control cells treated only with DMSO. Comparing to the cell treated with DMSO, all compounds were able to increase significantly the intensity of Mbl in the nuclei of DM1 myoblasts, especially compounds 6, 7, 8 and 9 at 1 microM. *P<0.05 (t-test).
Figure 7:
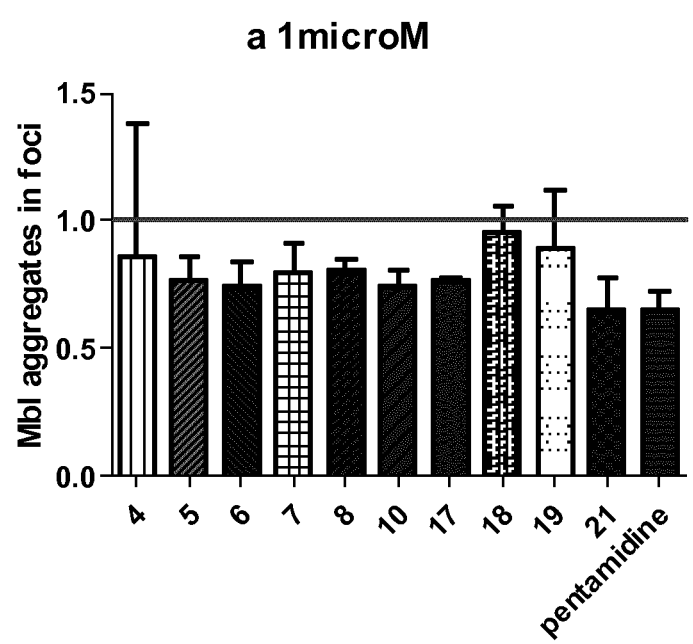
FIG. 7. Quantification of Mbl aggregates ribonuclear foci. Bar graphs show the mean±SEM of Mbl aggregates forming foci in DM1 myoblasts that had been treated at 1 microM concentration of compounds or solvent (DMSO) during one day. Horizontal red line marks the reference value of control cells treated only with DMSO. Comparing to pentamidine, which was used as positive control, all compounds decrease Mbl foci number at a similar degree than pentamidine. *P<0.05 (t-test).

See FIG. 6 and FIG. 7
Quantification of Foci

DM1 fibroblasts were seeded in a 94-well plate (8000 cell/per well) in standard media one day before adding the compounds to the media. Compounds were added to the cells at different concentrations, always maintaining the concentration of the solvent (DMSO) at 1% in the media. Every concentration of compound was tested in three different wells. 24 h after adding the compounds the cells were fixed with paraformaldehyde 4% in PBS and FISH to detect CUG RNA was performed using a (CAG)23 probe labelled with Cy3. Cells were counterstained with Hoechst to detect the nuclei. Incell 200 plate reader confocal was used for detection and quantification of the parameters selected and the data was analyzed using Graphpad software for statistical comparison of results.

Figure 5:
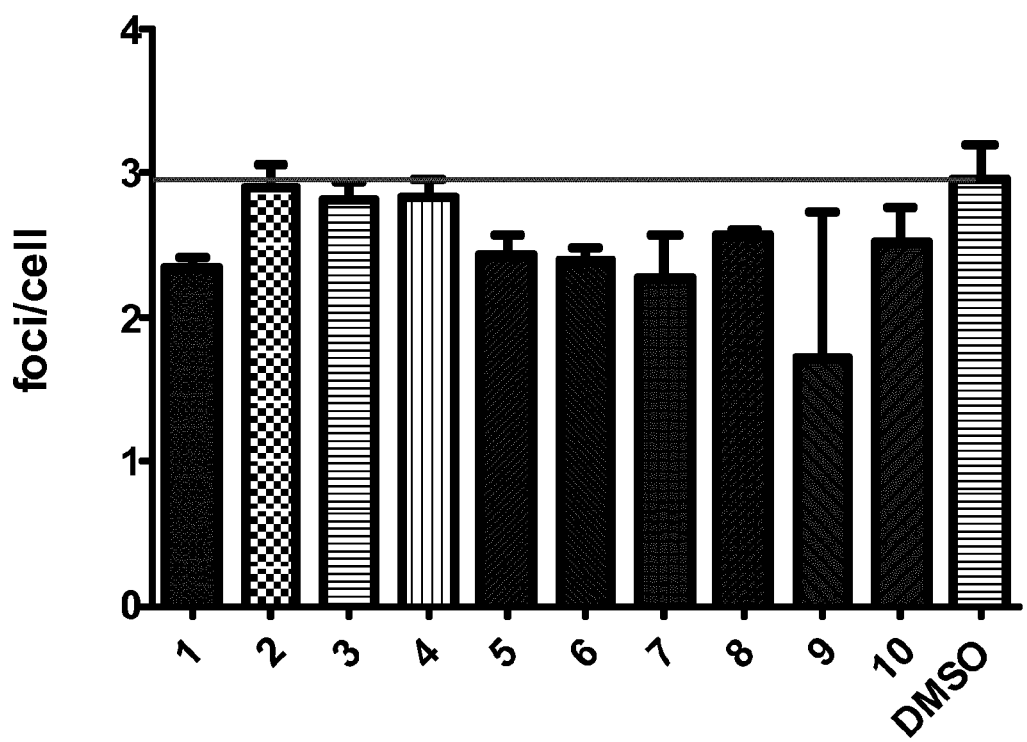
FIG. 5. Effect of compounds on foci number per cell in DM1 fibroblasts. Bar graphs show the mean±SEM foci number per nuclei in DM1 fibroblasts that had been treated at 100 microM of compounds (1-10) or solvent (DMSO) during one day. Horizontal red line marks the reference value of control cells treated only with DMSO. *P<0.05 (t-test).

See FIG. 5

Taken together these experiments show that xanthines have the ability to reduce the number of ribonuclear foci per cell. Such interference in the formation, stability or turnover of foci probably stems from their affinity for CUG repeat RNA. Because foci are a typical sign of RNA toxicity, their reduction supports the therapeutic use of xanthines in myotonic dystrophy. Moreover, xanthines increase MBNL1 in comparison to the positive control pentamidine. Because there is ample evidence that MBNL1 activity is limiting in DM1 and DM2 diseases due to sequestration by CUG and CCUG repeat expansions, that strategies aimed at increasing the amount of free MBNL1 are therapeutic in cell and animal experimentation models. Therefore, xanthines are proposed to be used in the treatment of DM1 and DM2 in patients.

Compositions Comprising at Least a Xanthine or Derivative Thereof Increase MBNL1 in Human DM1 Myoblasts To investigate whether compositions comprising at least a xanthine had an effect on MBNL1 expression levels in human cells we immunodetected MBNL1 in normal and control DM1 myoblasts, and in DM1 myoblasts grown in a range of combinations comprising at least a compound of formula (I) (see Table 3). MBNL1 expression increases in the cytoplasm and in the cell nucleus compared to DM1 myoblasts exposed to DMSO alone (used as solvent and negative control).

TABLE 3

| Sample | Component 1 | Component 2 | Component 3 | Relative ratio |
|---|---|---|---|---|
| 1 | Theophylline | Theobromine | — | 2:1 |
| 2 | Theophylline | Theobromine | — | 1:1 |
| 3 | Theophylline | Theobromine | — | 1:2 |
| 4 | Theophylline | Aminophylline | — | 2:1 |
| 5 | Theophylline | Aminophylline | — | 1:1 |
| 6 | Theophylline | Aminophylline | — | 1:2 |
| 7 | Theobromine | Aminophylline | — | 2:1 |
| 8 | Theobromine | Aminophylline | — | 1:1 |
| 9 | Theobromine | Aminophylline | — | 1:2 |
| 10 | Theobromine | Theophylline | Aminophylline | 1:1:1 |
| 11 | Theobromine | Theophylline | Aminophylline | 2:1:2 |
| 12 | Theobromine | Theophylline | Aminophylline | 1:1:2 |
| 13 | Theophylline | Theobromine | 1,7-Dimethylxanthine | 1:1:1 |
| 14 | Theophylline | Theobromine | 1,7-Dimethylxanthine | 2:1:2 |
| 15 | Theophylline | Theobromine | 1,7-Dimethylxanthine | 1:1:2 |
| 16 | Theobromine | Theophylline | 3-Isobutyl-1-methylxanthine | 1:1:1 |
| 18 | Theobromine | Theophylline | 3-Isobutyl-1-methylxanthine | 2:1:2 |
| 19 | Theobromine | Theophylline | 3-Isobutyl-1-methylxanthine | 1:1:2 |
| 20 | Theophylline | Theobromine | 3-Methylxanthine | 1:1:1 |
| 21 | Theophylline | Theobromine | 3-Methylxanthine | 2:1:2 |
| 22 | Theophylline | Theobromine | 3-Methylxanthine | 1:1:2 |
| 23 | Theobromine | Theophylline | 3-Ethyl-1-propylxanthine | 1:1:1 |
| 24 | Theobromine | Theophylline | 3-Ethyl-1-propylxanthine | 2:1:2 |
| 25 | Theobromine | Theophylline | 3-Ethyl-1-propylxanthine | 1:1:2 |
| 26 | Theobromine | 1,7-Dimethylxanthine | 3-Isobutyl-1-methylxanthine | 1:1:1 |
| 27 | Theobromine | 1,7-Dimethylxanthine | 3-Isobutyl-1-methylxanthine | 2:1:2 |
| 28 | Theobromine | 1,7-Dimethylxanthine | 3-Isobutyl-1-methylxanthine | 1:1:2 |
| 28 | Theobromine | 3-Isobutyl-1-methylxanthine | 3-Methylxanthine | 1:1:1 |
| 30 | Theobromine | 3-Isobutyl-1-methylxanthine | 3-Methylxanthine | 2:1:2 |
| 31 | Theobromine | 3-Isobutyl-1-methylxanthine | 3-Methylxanthine | 1:1:2 |
| 32 | Theobromine | 3-Isobutyl-1-methylxanthine | 3-Ethyl-1-propylxanthine | 1:1:1 |
| 33 | Theobromine | 3-Isobutyl-1-methylxanthine | 3-Ethyl-1-propylxanthine | 2:1:2 |
| 34 | Theobromine | 3-Isobutyl-1-methylxanthine | 3-Ethyl-1-propylxanthine | 1:1:2 |
| 35 | Theophylline | Caffeine | — | 2:1 |
| 36 | Theophylline | Caffeine | — | 1:1 |
| 37 | Theophylline | Caffeine | — | 1:2 |
| 38 | Theobromine | Caffeine | — | 2:1 |
| 39 | Theobromine | Caffeine | — | 1:1 |
| 40 | Theobromine | Caffeine | — | 1:2 |
| 41 | Aminophylline | Caffeine | — | 2:1 |
| 42 | Aminophylline | Caffeine | — | 1:1 |
| 43 | Aminophylline | Caffeine | — | 1:2 |
| 44 | Theophylline | Caffeine | Theobromine | 1:1:1 |
| 45 | Theophylline | Caffeine | Theobromine | 2:1:2 |
| 46 | Theophylline | Caffeine | Theobromine | 1:1:2 |
| 47 | 1,7-Dimethylxanthine | Caffeine | — | 2:1 |
| 48 | 1,7-Dimethylxanthine | Caffeine | — | 1:1 |
| 49 | 1,7-Dimethylxanthine | Caffeine | — | 1:2 |
| 50 | 3-Isobutyl-1-methylxanthine | Caffeine | — | 2:1 |
| 51 | 3-Isobutyl-1-methylxanthine | Caffeine | — | 1:1 |
| 52 | 3-Isobutyl-1-methylxanthine | Caffeine | — | 1:2 |
| 53 | 3-Methylxanthine | Caffeine | — | 2:1 |
| 54 | 3-Methylxanthine | Caffeine | — | 1:1 |
| 55 | 3-Methylxanthine | Caffeine | — | 1:2 |
| 56 | 3-Ethyl-1-propylxanthine | Caffeine | — | 2:1 |
| 57 | 3-Ethyl-1-propylxanthine | Caffeine | — | 1:1 |
| 58 | 3-Ethyl-1-propylxanthine | Caffeine | — | 1:2 |
| 59 | 1,7-Dimethylxanthine | 3-Isobutyl-1-methylxanthine | Caffeine | 1:1:1 |
| 60 | 1,7-Dimethylxanthine | 3-Isobutyl-1-methylxanthine | Caffeine | 2:1:2 |
| 61 | 1,7-Dimethylxanthine | 3-Isobutyl-1-methylxanthine | Caffeine | 1:1:2 |
| 62 | 3-Isobutyl-1-methylxanthine | 3-Methylxanthine | Caffeine | 1:1:1 |
| 63 | 3-Isobutyl-1-methylxanthine | 3-Methylxanthine | Caffeine | 2:1:2 |
| 64 | 3-Isobutyl-1-methylxanthine | 3-Methylxanthine | Caffeine | 1:1:2 |
| 65 | 3-Isobutyl-1-methylxanthine | 3-Ethyl-1-propylxanthine | Caffeine | 1:1:1 |
| 66 | 3-Isobutyl-1-methylxanthine | 3-Ethyl-1-propylxanthine | Caffeine | 2:1:2 |
| 67 | 3-Isobutyl-1-methylxanthine | 3-Ethyl-1-propylxanthine | Caffeine | 1:1:2 |

The invention claimed is:
1. A method for treating myotonic dystrophy type 1 or type 2 by reducing the severity of symptoms of myotonic dystrophy type 1 or type 2 in a subject suffering from myotonic dystrophy type 1 or type 2 by increasing the amount of free MBNL protein,
   wherein said symptoms include those affecting the heart, central nervous system, smooth muscle, hormonal system, immune system, vision, reproductive system, and skin, and
   wherein said method comprises administering to said subject a therapeutically effective amount of the compound of formula (I)

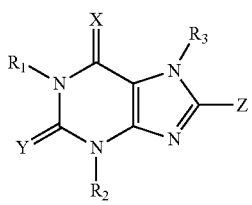

(I)

wherein:
$R^1$ is hydrogen or an optionally substituted alkyl chain;
$R^2$ is hydrogen, an optionally substituted alkyl chain, or an optionally substituted alkenyl;
$R^3$ is hydrogen, an optionally substituted alkyl chain, or a linker attached to another compound of formula (I) through N-7, being N-7 the N atom linked to $R^3$ in the structure of formula (I), wherein the linker is selected from an optionally substituted alkyl, an optionally substituted aryl, or an optionally substituted alkylarylalkyl;
X is O;
Y is O;
Z is hydrogen; an optionally substituted alkyl chain; or OH;
provided that the compound of formula (I) is not caffeine, and
provided that when $R^3$ is H, both $R^1$ and $R^2$ are not methyl.

2. The method of claim 1, wherein the compound used in said method is in the form of a tautomer, solvate, hydrate, a pharmaceutically acceptable salt thereof or forming oligomers.

3. The method of claim 1, wherein in the compound used in said method $R^1$, $R^2$, $R^3$ are independently each other H or Me, provided that when $R^3$ is H, both $R^1$ and $R^2$ are not methyl.

4. The method of claim 1, wherein in the compound used in said method $R^3$ is a linker as defined according to claim 1, for forming compounds with the following structure:

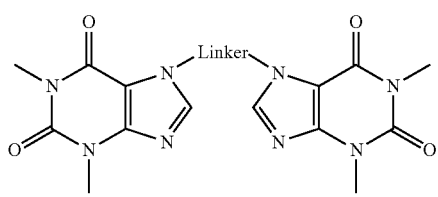

wherein the N to which the linker is bound is defined as N-7.

5. The method of claim 1, wherein the compound used in said method is selected from the group consisting of theobromine, xanthine, 1,7-dimethylxanthine, 3-isobutyl-1-methylxanthine, 3-methylxanthine, 3-ethyl-1-propylxanthine, 3-allyl-1-ethyl-8-hydroxyxanthine, 1-ethyl-3-isobutylxanthine,

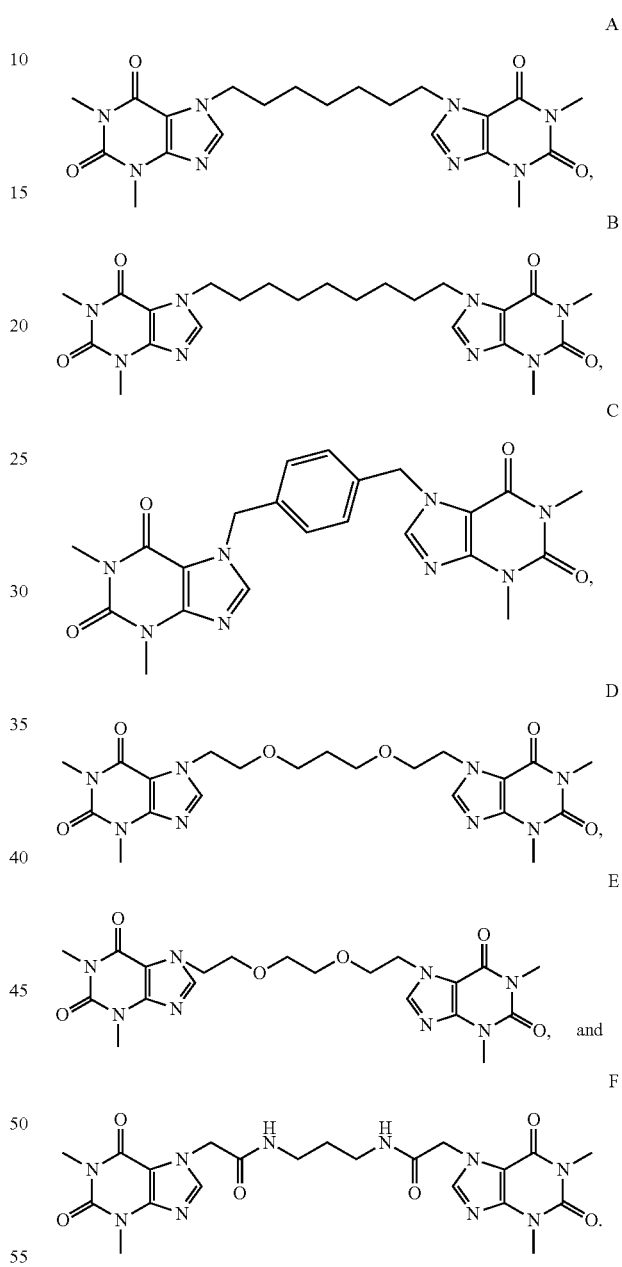

6. The method of claim 1, wherein the compound used in said method is included in a composition.

7. The method of claim 6, wherein the compound used in said method is included in a composition which is formulated as a pharmaceutical composition, food, food ingredient or supplement, nutraceutical composition, additive for a natural product or is present in the extract of a natural product.

8. The method of claim 6, wherein the compound used in said method is included in a composition which is present in a diary product, a beverage, a chocolate product or cereals.

9. The method of claim 6, wherein said composition is administered by oral, rectal, nasal, topical, vaginal, parenteral, transdermal, intraperitoneal, intrapulmonary or intranasal route.

10. The method of claim 6, wherein said composition is administered to a subject having a non-congenital form of DM.

11. The method of claim 1, wherein the compound used in said method is included in a composition which further comprises caffeine.

12. The method of claim 11, wherein the compound used in said method is included in a composition which is formulated as a pharmaceutical composition, food, food ingredient or supplement, nutraceutical composition, additive for a natural product or is present in the extract of a natural product.

13. The method of claim 12, wherein the compound used in said method is included in a composition which is present in a diary product, a beverage, a chocolate product or cereals.

14. The method of claim 12, wherein said composition is administered by oral, rectal, nasal, topical, vaginal, parenteral, transdermal, intraperitoneal, intrapulmonary or intranasal route.

15. The method of claim 12, wherein said composition is administered to a subject having a non-congenital form of DM.

16. The method of claim 1, wherein said compound is administered by oral, rectal, nasal, topical, vaginal, parenteral, transdermal, intraperitoneal, intrapulmonary or intranasal route.

17. The method of claim 1, wherein said compound is administered to a subject having a non-congenital form of DM.

18. The method of claim 1, wherein said subject is a human subject.

* * * * *